(12) United States Patent
Ghobrial

(10) Patent No.: US 10,173,023 B1
(45) Date of Patent: Jan. 8, 2019

(54) OROPHARYNGEAL DEVICE

(71) Applicant: Victor G. Ghobrial, Bradenton, FL (US)

(72) Inventor: Victor G. Ghobrial, Bradenton, FL (US)

( * ) Notice: Subject to any disclaimer, the term of this patent is extended or adjusted under 35 U.S.C. 154(b) by 527 days.

(21) Appl. No.: 14/616,967

(22) Filed: Feb. 9, 2015

Related U.S. Application Data

(60) Provisional application No. 61/937,087, filed on Feb. 7, 2014.

(51) Int. Cl.
*A61M 16/04* (2006.01)
*A61M 16/10* (2006.01)
*A61M 16/20* (2006.01)
*A61M 16/06* (2006.01)

(52) U.S. Cl.
CPC .... *A61M 16/0497* (2013.01); *A61M 16/0463* (2013.01); *A61M 16/0683* (2013.01); *A61M 16/1005* (2014.02); *A61M 16/20* (2013.01); *A61M 2202/0208* (2013.01); *A61M 2230/432* (2013.01)

(58) Field of Classification Search
CPC .............. A61M 16/00; A61M 16/04–16/0497
See application file for complete search history.

(56) References Cited

U.S. PATENT DOCUMENTS

| | | | |
|---|---|---|---|
| D261,442 S | 10/1981 | Anderson | |
| 5,590,643 A * | 1/1997 | Flam ................. | A61M 16/0488 128/200.26 |
| 5,682,880 A | 11/1997 | Brain | |
| 5,976,072 A | 11/1999 | Greenberg | |
| 6,568,388 B2 | 5/2003 | Christopher | |
| 6,729,325 B2 | 5/2004 | Alfery | |
| 7,263,997 B2 | 9/2007 | Madsen et al. | |
| 7,278,420 B2 | 10/2007 | Ganesh et al. | |
| 7,866,313 B2 | 1/2011 | Isenberg et al. | |
| 8,028,704 B2 | 10/2011 | Reynolds, II et al. | |
| 8,220,461 B1 | 7/2012 | Guerra et al. | |
| 8,413,658 B2 | 4/2013 | Williams | |
| 2002/0095118 A1* | 7/2002 | Bertoch ............ | A61M 16/0488 604/174 |
| 2010/0030027 A1 | 2/2010 | Bastid et al. | |
| 2010/0051024 A1 | 3/2010 | Abrons | |
| 2011/0265798 A1* | 11/2011 | Maguire ............... | A61M 16/04 128/207.14 |
| 2013/0014754 A1 | 1/2013 | Guerra et al. | |

(Continued)

*Primary Examiner* — Rachel T Sippel
(74) *Attorney, Agent, or Firm* — Frijouf, Rust & Pyle, P.A.

(57) ABSTRACT

An oropharyngeal device is disclosed for insertion into the oral cavity and the oropharynx of an individual. The oropharyngeal device comprises a tubular member extending between a proximal end and a distal end. The tubular member includes a channel extending between the primary aperture and the secondary aperture. A flange is coupled to the proximal end of the tubular member. The tubular member defines a gradual narrowing of the tubular member between the proximal end and the distal end for avoiding gagging reflex of the individual upon insertion of the distal end of the tubular member through the oral cavity and positioned adjacent to the epiglottis. The tubular member defines an arcuate shape for depressing the tongue and maintaining airway patency between the oral cavity and the epiglottis.

12 Claims, 41 Drawing Sheets

(56) References Cited

U.S. PATENT DOCUMENTS

| | | | |
|---|---|---|---|
| 2013/0030249 A1 | 1/2013 | Vazales et al. | |
| 2013/0037026 A1* | 2/2013 | Miller | A61M 16/04 128/204.18 |
| 2014/0323896 A1* | 10/2014 | McCauley | A61M 16/0486 600/531 |
| 2014/0366887 A1* | 12/2014 | Zhao | A61M 16/0488 128/207.14 |

* cited by examiner

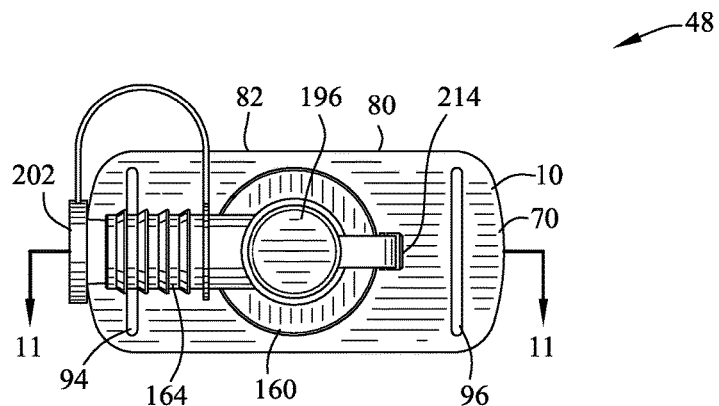
FIG. 9
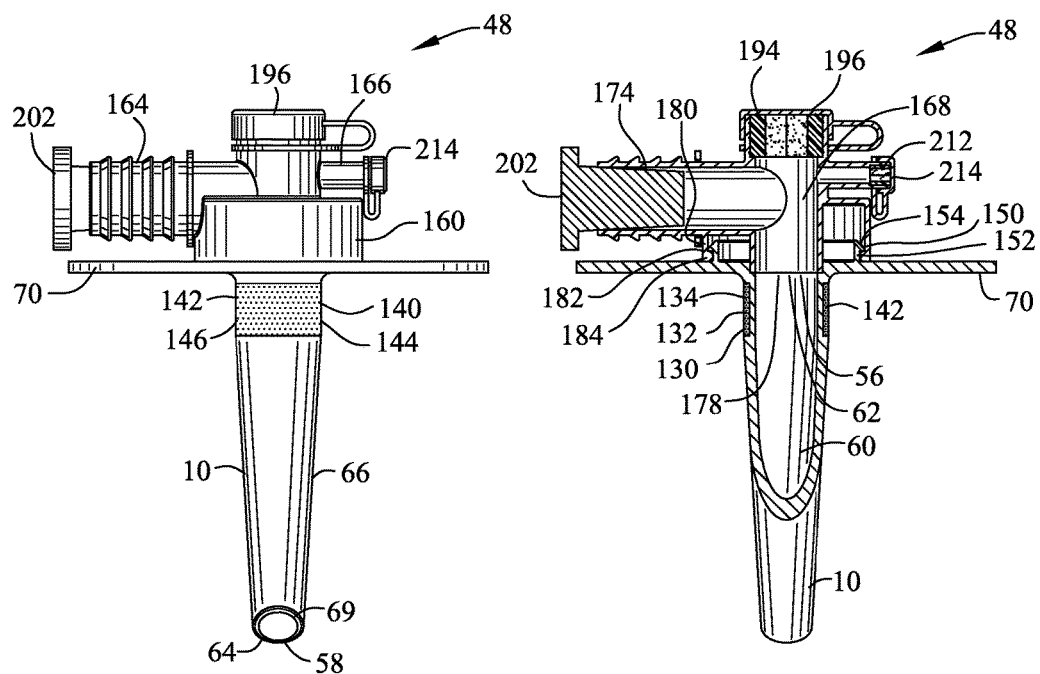
FIG. 10
FIG. 11

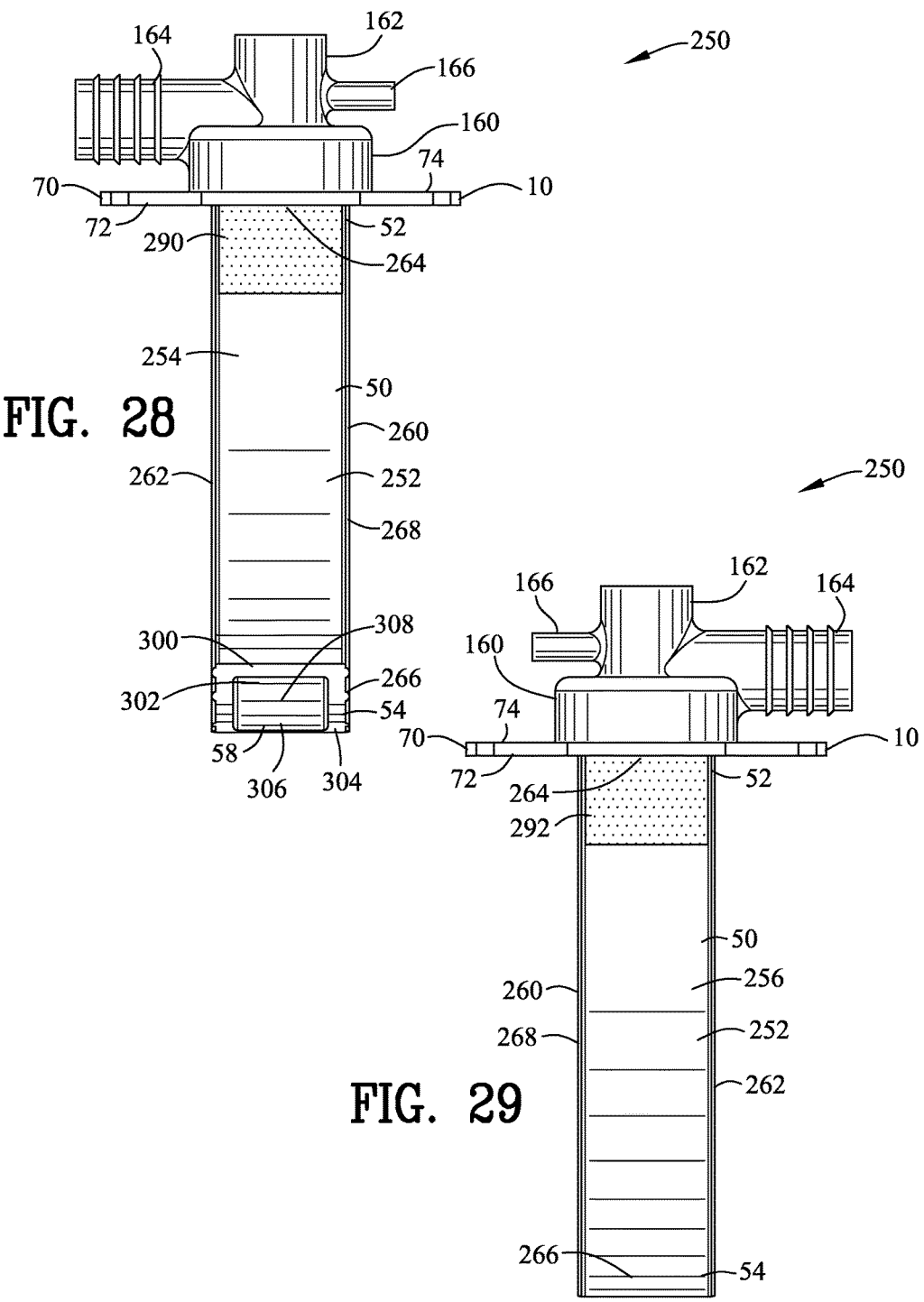

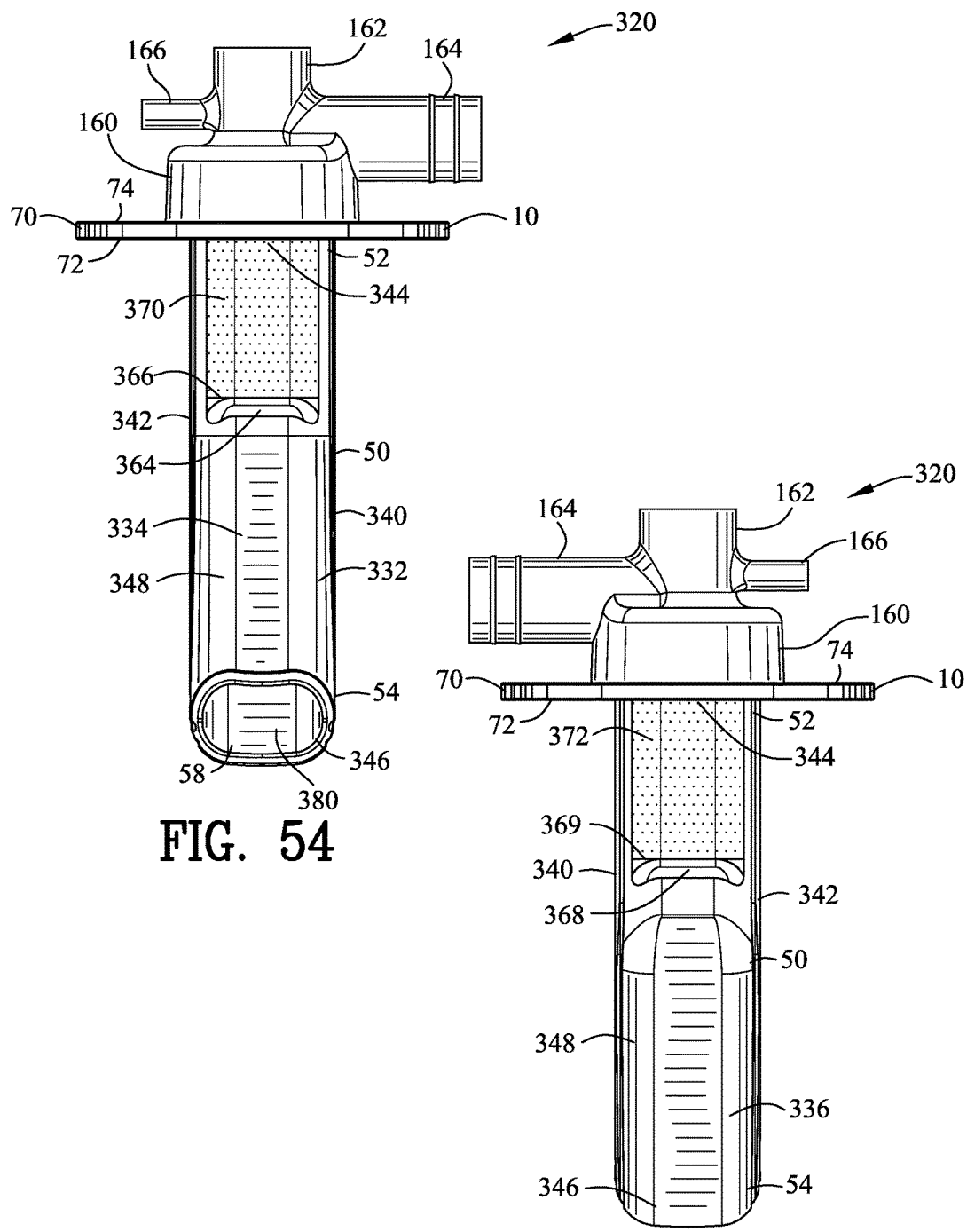

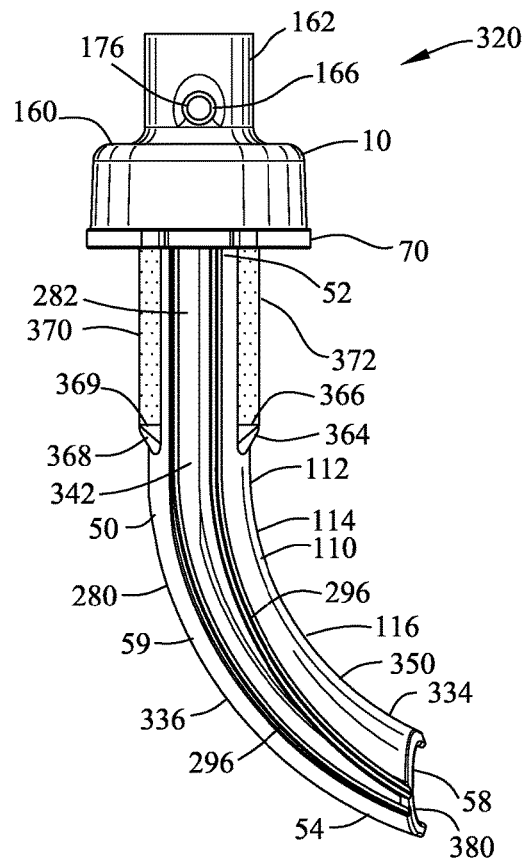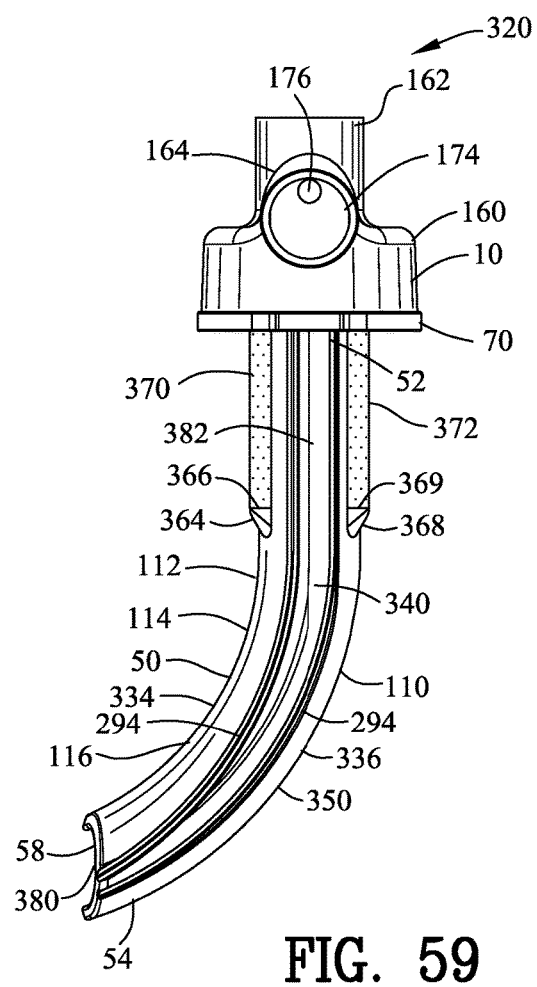
FIG. 58
FIG. 59

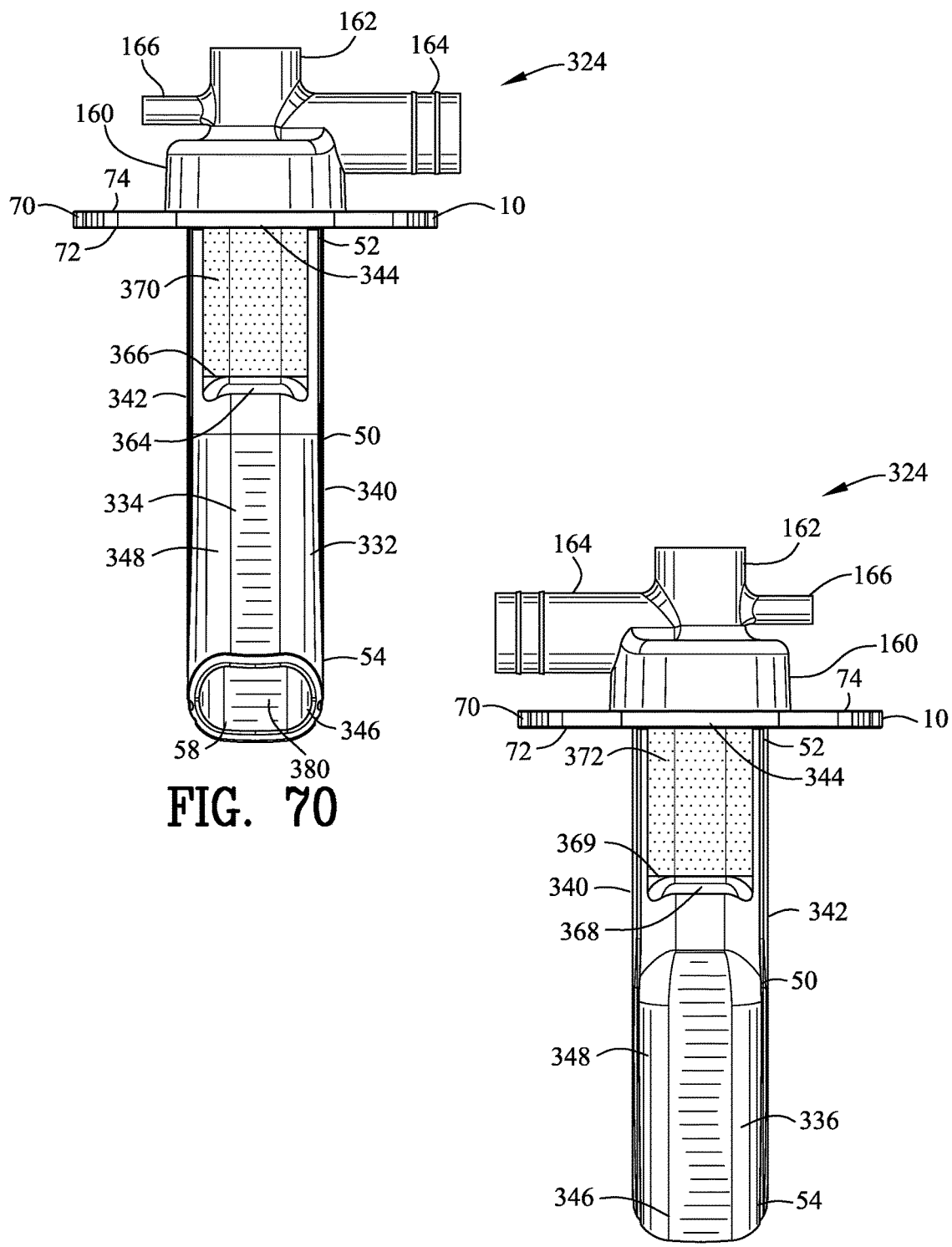

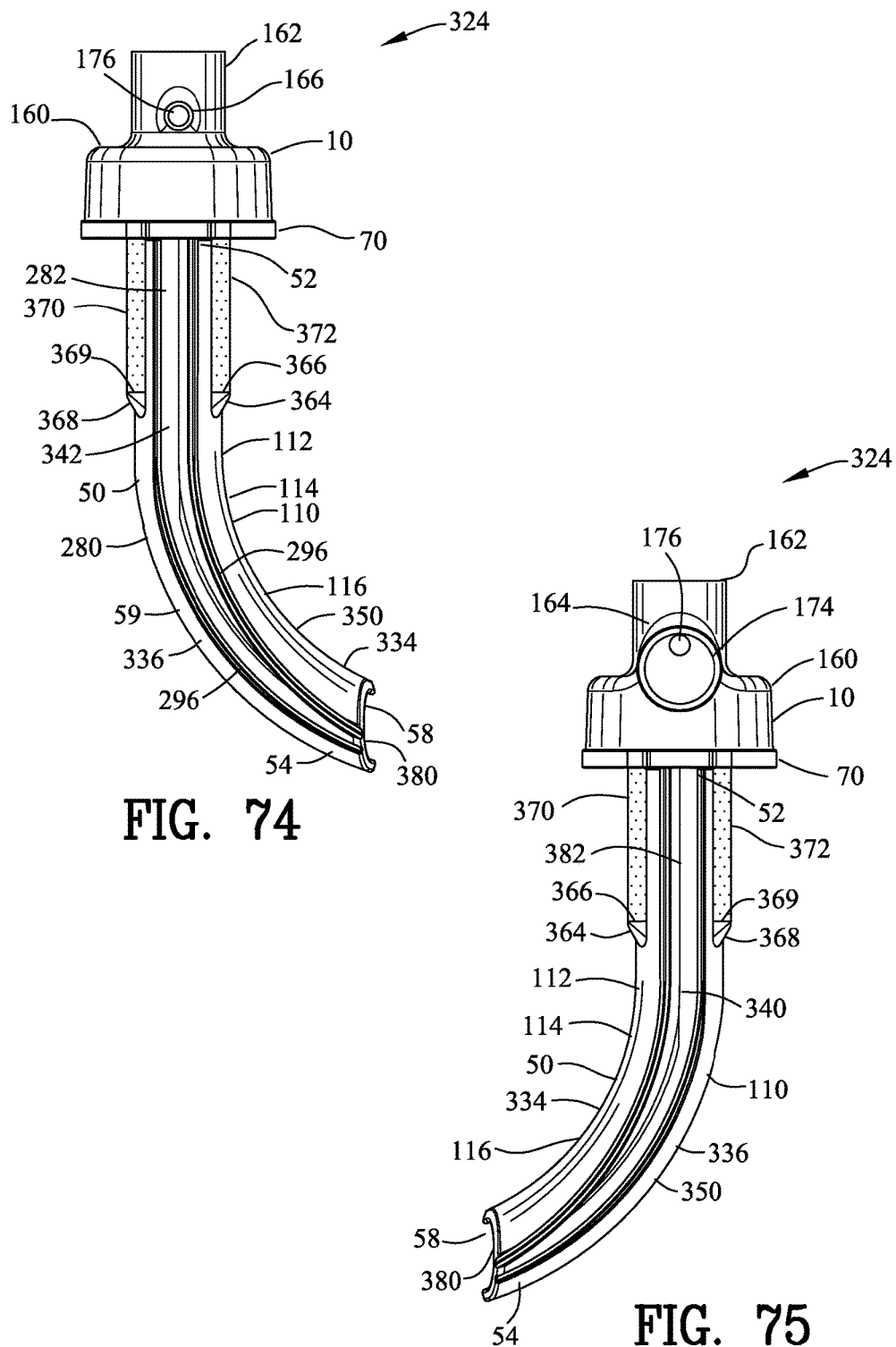

OROPHARYNGEAL DEVICE

CROSS-REFERENCE TO RELATED APPLICATIONS

This application claims benefit of U.S. Patent Provisional application No. 61/937,087 filed Feb. 7, 2014. All subject matter set forth in provisional application No. 61/937,087 is hereby incorporated by reference into the present application as if fully set forth herein.

BACKGROUND OF THE INVENTION

Field of the Invention

This invention relates to oral airway management and more particularly to an oropharyngeal device for insertion into the oral cavity and the oropharynx of an individual.

Background of the Invention

For many years prior to the late 19th century, tracheotomy was considered the only reliable method for tracheal intubation. Physicians undertook tracheotomy only as a last resort since patient survival rates were extremely poor. By the late 19th century, advances in the understanding of anatomy and germ theory of disease increased survival rates to an acceptable level to make tracheotomy an acceptable treatment option.

During the same time period, the development of endoscopic instrumentation had improved to a great degree. Direct laryngoscopy became a reasonable means to achieve a secure airway. By the mid 20th century, endoscopy and non-surgical tracheal intubation had become an essential component in the practices of anesthesiology, gastroenterology, and laryngology.

Tracheal intubation can be associated with minor complications such as broken teeth or minor lacerations of upper airway tissues, but more importantly more serious, potentially fatal complications such as pulmonary aspiration of stomach contents, and unrecognized intubation of the esophagus can lead to potentially fatal anoxia. Additionally, other variables such as unusual airway anatomy or other variables require the practitioner to evaluate alternative strategies for securing the airway.

Modern tracheal intubation devices offer a variety of features which permit viewing, administration of medications, anesthetics as well as providing a breathing conduit. There have been many in the prior art who have attempted to solve the problems associated with tracheal intubation with varying degrees of success. None, however completely satisfies the requirements for a complete solution to the aforestated problem. The following U. S. Patents are attempts of the prior art to solve this problem.

U.S. Pat. No. 5,682,880 to Brain discloses an intubating laryngeal-mask airway device which compresses a flexible airway tube with conventional distal-end mask structure, wherein one or more relatively stiff and suitably curved reinforcement elements determine the curvilinear course of the airway tube and are removably embodied in the flexible airway tube. An external handle connected to the proximal end of the one or more reinforcement elements facilitates rapid installation of the mask, and removal of the one or more reinforcement elements exposes guide passages well suited to subsequent introduction of fiber-optic devices for visual inspection of the entrance to the trachea, whereby to assure properly directed passage of an endotracheal tube or other instrumentation into the trachea. Optional provision is made for use of a reinforcement-guide system to serve another fiber-optic device having viewing exposure directed toward the esophagus, thereby providing a visible clue of a misdirected endotracheal tube before it can do any damage in a region which must be avoided.

U.S. Pat. No. 5,976,072 to Greenberg discloses a method for fiberoptic endotracheal intubation that uses a device having a cannula with a first, distal end for placement within the pharynx of a patient, a second, proximal end for being disposed outside of the patient's oral cavity, and a flow passage between the first and second ends. The cannula has a length such that, when the distal end is placed within the pharynx, it terminates distally at a point near the patient's epiglottis. The device includes an inflatable cuff structure for forming a seal between a wall of the cannula and the patient's pharynx. The cuff is positioned adjacent to the distal end of the device and defines, on inflation, a ventral/anterior portion and a posterior portion. The method involves a step of inserting the device, with cuff deflated, into a patient's mouth so that the distal end of the device is disposed at a point near the patient's epiglottis to establish an airway column down the core of the device. Once the cuff structure is inflated, the patient's airway is supported to provide spontaneous breathing and controlled ventilation through the flow passage of the device. Then, a fiberoptic scope, on which an endotracheal tube has been preloaded so that the distal tip of the scope projects beyond the endotracheal tube, is inserted into the patient through the patient's oral cavity so that the lip is in the throat past the uvula, whereby after insertion of the device and insertion of the fiberoptic scope, the scope is disposed exteriorly of the device. Then, the tip of the fiberoptic scope is advanced so that it enters the trachea. The endotracheal tube is then advanced through the oral cavity and into the trachea using the fiberoptic scope as a guide. Finally, the fiberoptic scope is removed from the trachea.

U.S. Pat. No. 6,568,388 to Christofer discloses a method and apparatus for guiding insertion of an endotracheal tube into a patient's trachea simultaneously allows a continued supply of air/oxygen to be delivered into the patient's airway and lungs. A guide having a curved distal portion is inserted into the patient's mouth and hypopharynx. A second lumen extending along the guide is used to supply air/oxygen into the patient's airway and to flush carbon dioxide from the lungs. A fiber optic probe is inserted through an endotracheal tube and this assembly is advanced along the guide into the patient's airway, while ventilation continues without interruption through the second lumen. The direction of the distal tip of the fiber optic probe can be controlled by the physician. This allows the physician to carefully guide the fiber optic probe and endotracheal tube to a position past the larynx while ventilation continues. After the distal end of the fiber optic probe has guided the endotracheal tube past the larynx and into the trachea, the guide and mask are withdrawn over the fiber optic probe. The fiber optic probe can used to monitor the position of the distal end of the endotracheal tube during this step to ensure that it remains in position. The fiber optic probe is then removed from within the endotracheal tube. The cuff on the endotracheal tube is inflated and a ventilator is connected to the proximal end of the endotracheal tube to ventilate the patient.

U.S. Pat. No. 7,263,997 to Madsen et al. discloses a respiratory apparatus including an instrument introduction section that is used for introducing an instrument into an artificial airway of a patient. The instrument introduction section has a distal end and proximal end with an opening which allows for insertion of the instrument into the instrument introduction section. The instrument is movable through the passageway in the instrument introduction section between the proximal and distal ends. A valve is located in the instrument introduction section and has a closed position in which the instrument may be isolated from the artificial airway of the patient. The valve at least substantially blocks the passageway of the instrument introduction section when in the closed position. The valve also has an open position that allows for the instrument to be advanced through the instrument introduction section. A manifold is attached to the distal end of the instrument introduction section. The manifold is in communication with the artificial airway of the patient.

U.S. Pat. No. 7,278,420 to Armstead et al. discloses an oropharyngeal device for insertion into the mouth of a patient. The device includes a body having a distal end and a proximal end with a flange formed at the proximal end. The distal end is inserted into the mouth until the flange is disposed outside and adjacent to the patient's mouth. The flange keeps the proximal device from entering the mouth. The body is sized such that the distal end of the body is disposed within the pharynx above the epiglottis. The device includes a channel that forms an airway between the ends. The device also includes at least three separate conduits integrated into the body for administering oxygen, suctioning, and for assessing ventilation thorough end-tidal carbon dioxide monitoring. The conduits for oxygenation and suctioning extend through the body between its proximal and distal ends. The conduit for end-tidal carbon dioxide monitoring terminates within the channel.

U.S. Pat. No. 6,729,325 to Alfrey discloses an oral airway including an elongate tubular member having a distal and a proximal end. The oral airway is configured to place the distal end in a supraglottic position when operatively placed within the hypopharynx of a patient. A temperature sensor is operatively associated with the elongate tubular member to detect a core temperature of a patient with the distal end of the oral airway operatively placed in a superglottic position within the hypopharynx of the patient.

U.S. Pat. No. 7,866,313 B2 to Hoy et al. discloses an oral airway including a first component having a first guiding surface and a second component having a second guiding surface. The first component and the second component are adapted to be removably coupled together such that the first guiding surface and the second guiding surface collectively define and encompass an interior passage through the oral airway that is dimensioned to direct, for example, a fiber-optic scope or an endotracheal tube extending through the interior passage for tracheal intubation. The first and second components are configured to be decoupled and independently removed from a patient's mouth without disrupting an endotracheal tube that has been extended through the conduit for tracheal intubation. The first and second components may be maintained in coupled disposition by an interlocking mechanical structure. The first and second components also may be maintained in coupled disposition by magnetism.

U.S. Pat. No. 8,028,704 B2 to Flaker et al. discloses a bite block that is inserted into a patient's mouth during an endoscopic diagnostic or surgical procedure that has a channel for receiving an endoscope or other surgical instrument through the patient's mouth and additional channels transmitting a gas to the patient and transmitting expired gas from the patient.

U.S. Pat. No. 8,220,461 to Guerra et al discloses an oral airway for insertion into the mouth and pharynx of a patient and adapted to connect to an anesthesia breathing connector, a suction tube, or a nasal cannula, interchangeably as needed, without necessitating the removal of the oral airway from the patient. A tubular member has a connector at a proximal end and includes a first portion that is adapted for fixing with the anesthesia breathing connector. A second portion of the connector is adapted for receiving the suction tube. At least one protuberance between the first and second portions receives and retains a portion of the nasal cannula, or alternately, at least one aperture is included in the second portion for receiving a portion of the nasal cannula. A mouth guard extends outwardly from the connector. Alternately, a suction tube guide within the tubular member may be slidably positionable between a retracted and extended position.

U.S. Pat. No. 8,413,658 to Williams discloses an oral airway providing a patent airway to a patient, supplies oxygen to the patient and monitors expelled gases during endoscopic or intubating procedures. The oral airway includes a central lumen and two lateral breathing channels. A bracket at the proximal end of the oral airway functions to guide an oxygen supply line and an end tidal carbon dioxide monitoring line into the lateral breathing channels and to act as a barrier beyond which the airway cannot be inserted into the mouth of the patient. The airway has a straight main central lumen which serves as a guide and conduit to facilitate endoscope, bronchoscope, or fiber optic bronchoscope placement and manipulation.

United States Patent Application 20100030027 to Bastid et al. discloses an intraoral medical device comprising: a mouth opener formed by a tubular element arranged to define an access to the oral cavity of the patient. A tongue depressor which is designed to be inserted removably into the tubular element and having a channel through which a breathable gas is injected opens out at the distal end of said tongue depressor. The device includes a conduit through which surgical instruments are passed and which opens out at the distal end of said tongue depressor. The mouth opener comprises an injection conduit designed to be connected to a source of breathable gas and configured to inject said gas into the oral cavity of the patient when the tongue depressor is not inserted in the tubular element and to inject said gas into the injection channel of said tongue depressor when the latter is inserted in said tubular element.

United States Patent Application 20100051024 A1 to Abrons discloses an oral airway comprised of two articulating parts which displace the tongue anteriorly and stent open the oropharynx. This device reversibly locks in a conformation which allows it to be used as a conduit for a fiberoptic scope or other airway device. An adjunct to airway management which can be used when mask ventilation or endotracheal intubation is indicated and can be removed easily after intubation without manipulation of the endotracheal tube. Other embodiments are described as shown.

United States Patent Application 20130014754 to Guerra et al. discloses an oral airway for insertion into a mouth and pharynx of a patient to provide a breathing pathway and for cooperating with either an anesthesia breathing connector, a suction tube, or a nasal cannula. The oral airway includes a first tubular member, a second tubular member disposed within the first tubular member, and a connector configured to securely attach to both the first tubular member and the second tubular member. The connector includes a first portion in fluid communication with the first tubular member and a second portion in fluid communication with the second tubular member.

United States Patent Application 20130030249 to Vazales et al. discloses systems, methods, and devices for facilitating insertion of an endotracheal tube and/or for verifying the position of the endotracheal tube within an airway of a patient with respect to an anatomical landmark of a patient. Systems, methods, and devices for facilitating removal of debris from the distal airways of a patient under direct visualization are also disclosed.

Although the aforementioned prior art have contributed to the development of the art of securing an object to a support member, none of these prior art patents have solved the needs of this art.

Therefore, it is an object of the present invention to provide an improved apparatus for tracheal intubation.

Another object of this invention is to provide an improved apparatus for introducing a fiber optic device and securing airway patency and connection to oxygen via a side channel.

Another object of this invention is to provide an improved apparatus that is simple for the operator to use.

Another object of this invention is to provide an improved apparatus that is easy to cost effectively produce.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an oropharyngeal device for insertion into the oral cavity and the oropharynx of an individual. The oral cavity includes a tongue and the oropharynx includes an epiglottis. The oropharyngeal device comprises a tubular member extending between a proximal end and a distal end. The proximal end of the tubular member defines a primary aperture. The distal end of the tubular member defines a secondary aperture. The tubular member includes a channel extending between the primary aperture and the secondary aperture. A flange includes a lower surface and an upper surface. The lower surface of the flange is coupled to the proximal end of the tubular member. The flange includes a flange aperture adjacent to the primary aperture. The primary aperture defines a first circumference. The secondary aperture defines a second circumference. The first circumference is greater than the second circumference for defining a gradual narrowing of the tubular member between the proximal end and the distal end for avoiding gagging reflex of the individual upon insertion of the distal end of the tubular member through the oral cavity and positioned adjacent to the epiglottis. The tubular member defines an arcuate shape for depressing the tongue and maintaining airway patency between the oral cavity and the epiglottis.

In a more specific embodiment of the invention, the proximal end of the tubular member includes an inset channel. The inset channel has a channel depth and a channel width. A deformable annular body has a body thickness and a body width. The deformable annular body is positioned within the inset channel for engaging with the teeth of the individual. The channel depth and the body thickness are equivalent and the channel width and the body width are equivalent for defining a flush and a continuous transition between the tubular member and the deformable annular body.

In one embodiment of the invention, the upper surface of the flange includes circular locking rim. A manifold includes an input device cylindrical body, a gaseous cylindrical body and a main cylindrical body. The input device cylindrical body defines an input device aperture. The gaseous cylindrical body defines a gaseous aperture. The main cylindrical body defines an output aperture. The manifold includes a locking cap for engaging with the circular locking rim with the output aperture adjacent to the flange aperture and permitting a rotational displacement of the manifold relative to the flange. The gaseous aperture provides a source of oxygen supplement through the tubular member and into the oral cavity. A sphincter valve is positioned within the input device aperture for permitting the insertion of an elongated device through the tubular member and into the epiglottis and preventing the loss of the source of oxygen supplement.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 9 is a view similar to FIG. 3 illustrating an input device cap engaging with an input device aperture and a gaseous cap engaging with a gaseous aperture;

FIG. 10 is a front view of FIG. 9;

FIG. 11 is a sectional view along line 11-11 in FIG. 9;

FIG. 28 is a front view of a second embodiment of the oropharyngeal device of the present invention;

FIG. 29 is a rear view of FIG. 28;

FIG. 54 is a front view of a third embodiment of the oropharyngeal device of the present invention;

FIG. 55 is a rear view of FIG. 54;

FIG. 58 is a left side view of FIG. 54;

FIG. 59 is a right side view of FIG. 54;

FIG. 70 is a front view of a fifth embodiment of the oropharyngeal device of the present invention;

FIG. 71 is a rear view of FIG. 70;

FIG. 74 is a left side view of FIG. 70;

FIG. 75 is a right side view of FIG. 70;

Similar reference characters refer to similar parts throughout the several Figures of the drawings.

DETAILED DISCUSSION

Figure 1:
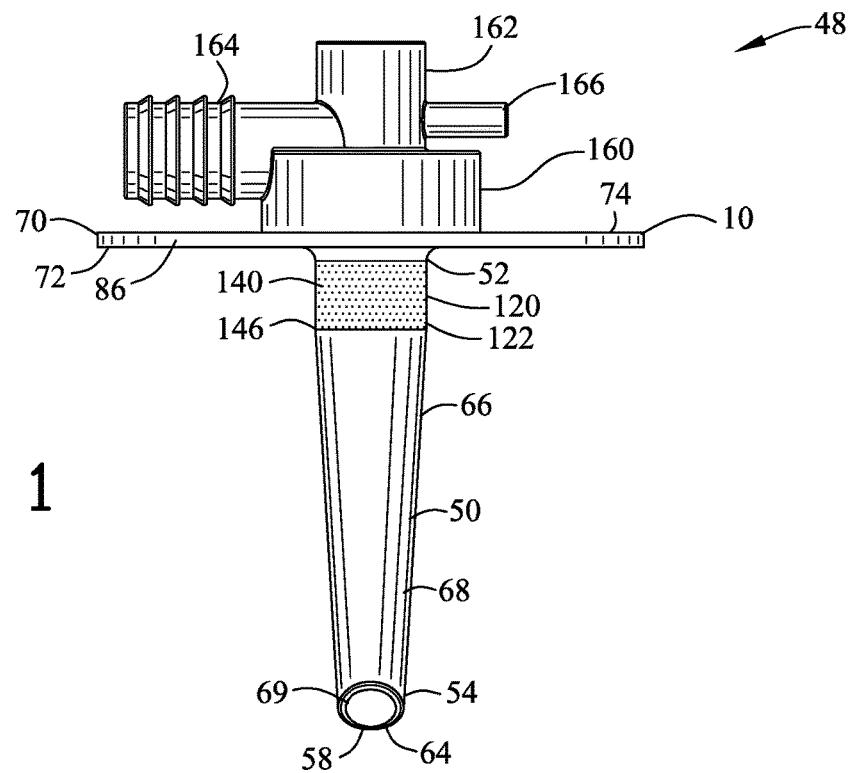
FIG. 1 is a front view of an oropharyngeal device of the present invention.
Figure 2:
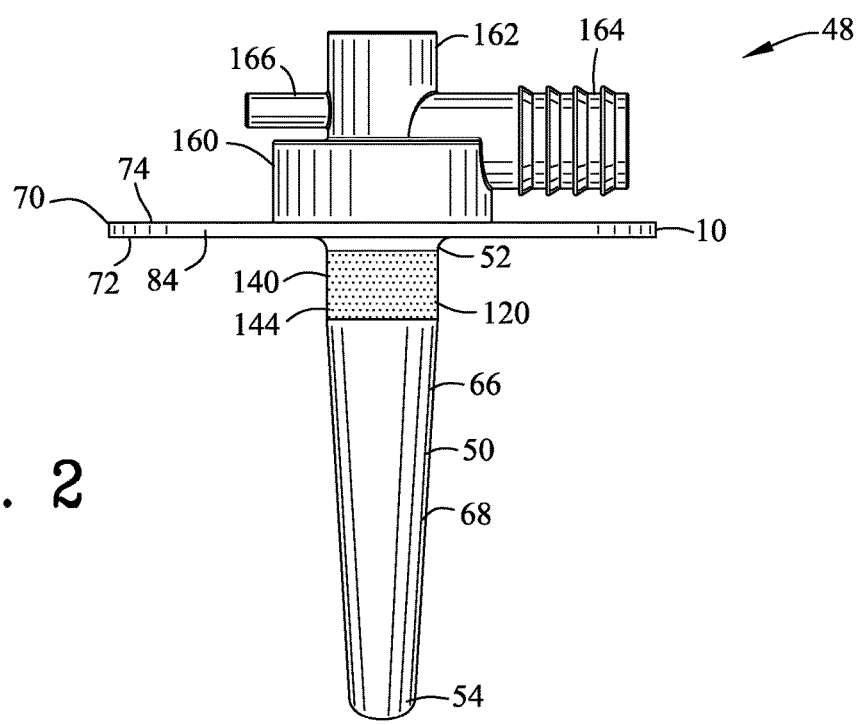
FIG. 2 is a rear view of FIG. 1.
Figure 3:
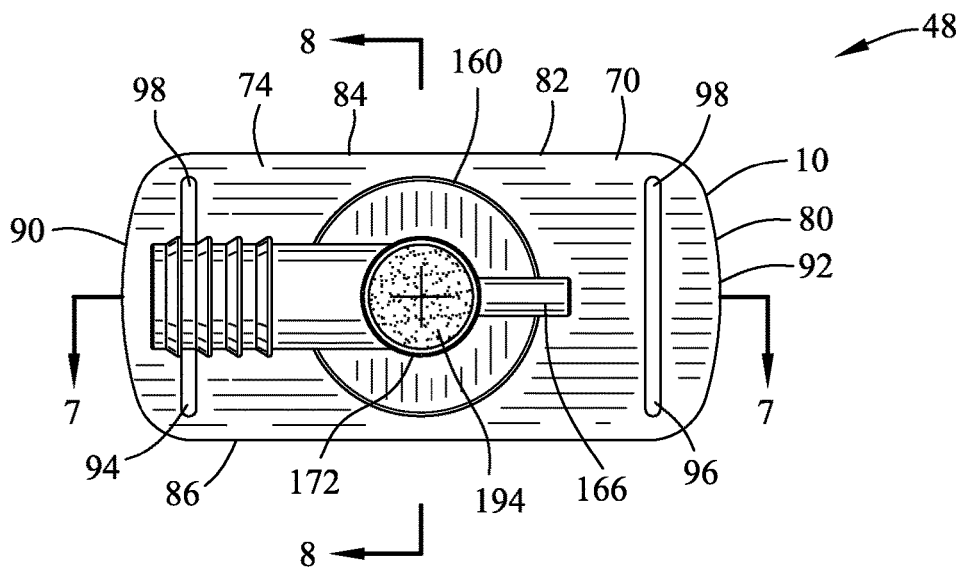
FIG. 3 is a top view of FIG. 1.
Figure 4:
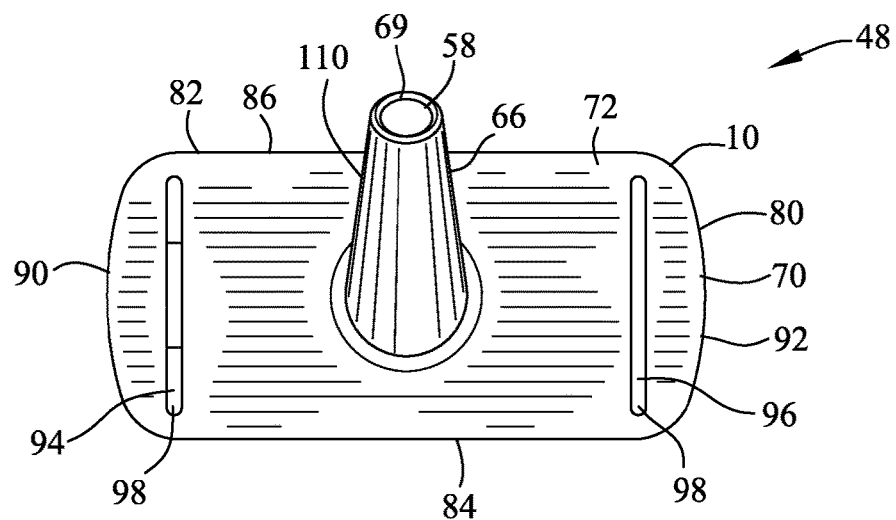
FIG. 4 is a bottom view of FIG. 1.
Figure 85:
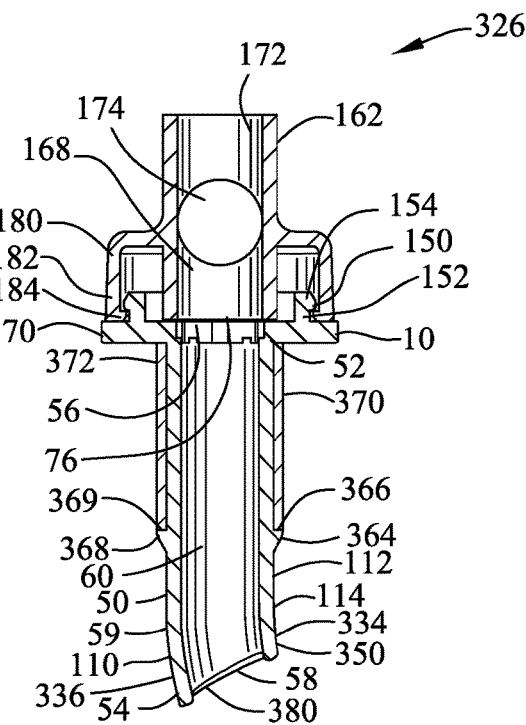
FIG. 85 is a sectional view along line 85-85 in FIG. 80.

FIGS. 1-85 illustrate an oropharyngeal device 10 for insertion into the oral cavity 20 and the oropharynx 22 of an individual 24. As best shown in FIGS. 13, 15, 16, 19, 26, 40, 42, 43, 4649 and 51, the oral cavity 20 includes a tongue 26. The oropharynx 22 includes an epiglottis 28.

FIGS. 1-85 illustrate the oropharyngeal device 10 comprises a tubular member 50 extending between a proximal end 52 and a distal end 54. The proximal end 52 of the tubular member 50 defines a primary aperture 56. The distal end 54 of the tubular member 50 defines a secondary aperture 58. The tubular member 50 includes a channel 60 extending between the primary aperture 56 and the secondary aperture 58.

A flange 70 includes a lower surface 72 and an upper surface 74. The lower surface 72 of the flange 70 is coupled to the proximal end 52 of the tubular member 50. The flange 70 includes a flange aperture 76 adjacent to the primary aperture 56. The flange 70 includes a circumference edge 80 that may define a generally shaped rectangle 82 as shown in FIGS. 1-27. More specifically, the generally shaped rectangle 82 includes a first linear edge 84 oppositely opposed to a second linear edge 86 and a first arcuate edge 90 oppositely opposed to a second arcuate edge 92. The flange 70 is configured such that the first linear edge 84 is positioned adjacent to the nose 30 of the individual 24. The generally shaped rectangle 82 permits the flange 70 to abut the upper lips 32 and lower lips 34 for provide a stable engagement between the oropharyngeal device 10 and the individual 24, while also permitting access to the remainder of the face 36 including the nose 30.

The flange 70 may further include a first strap groove 94 and a second strap groove 96. Preferably, the first strap groove 94 is positioned adjacent to the first arcuate edge 90 and the second strap groove 96 is positioned adjacent to the second arcuate edge 92. The first strap groove 94 and the second strap groove 96 define an oppositely opposed position 98 relative to the flange aperture 76. An elastic band 100 engages the first strap groove 94 and the second strap groove 96 for encircling the head 40 or neck 42 of the individual 24 and maintaining the flange 70 adjacent to the oral cavity 20 of the individual 24.

As best shown in FIGS. 21-25, the combination of the generally shaped rectangle 82 and the first strap groove 94 and the second strap groove 96 being positioned adjacent to the first arcuate edge 90 and the second arcuate edge 92 respectively, positions the elastic band 100 for defining a first generally linear band portion 102 between the first arcuate edge 90 and the neck 42 and a second generally linear band portion 104 between the second arcuate edge 92 and the neck 42. The first generally vertical band 102 and the second generally vertical band 104 assist in maintaining the flange 70 in an abutted positioned against the upper lips 32 and lower lips 34 for providing a stable engagement between the oropharyngeal device 10 and the individual 24.

FIGS. 1-27 illustrate a first embodiment 48 of the present invention. The primary aperture 56 defines a first circumference 62. The secondary aperture 58 defines a second circumference 64. The first circumference 62 is greater than the second circumference 64 for defining a gradual narrowing 66 or tapering 68 of the tubular member 50 between the proximal end 52 and the distal end 54. Preferably, the tubular member 50 defines a circular cross-section 69 between the proximal end 52 and the distal end 54. However, the tubular member 50 may have an elliptical, generally rectangle or other cross-section shapes.

Figure 5:
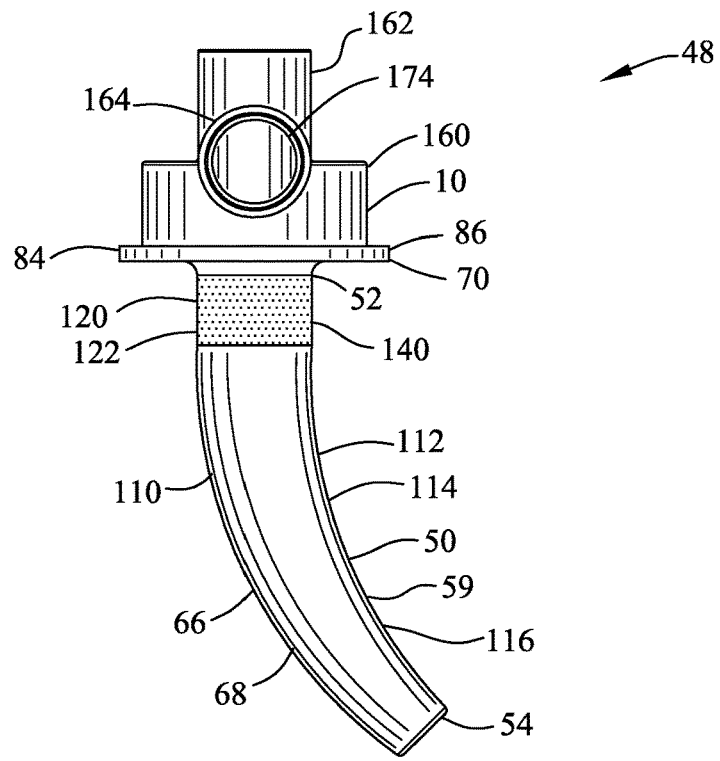
FIG. 5 is a left side view of FIG. 1.
Figure 6:
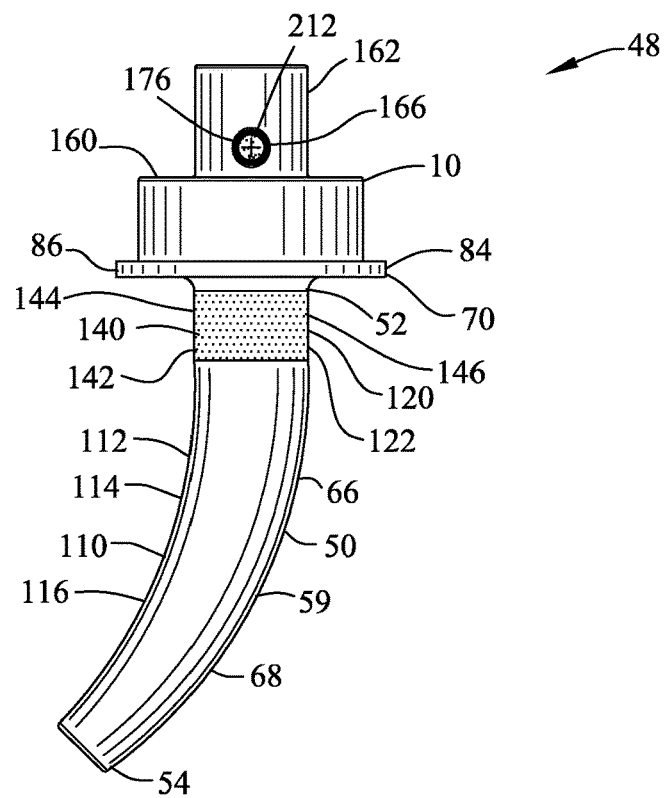
FIG. 6 is a right side view of FIG. 1.
Figure 7:
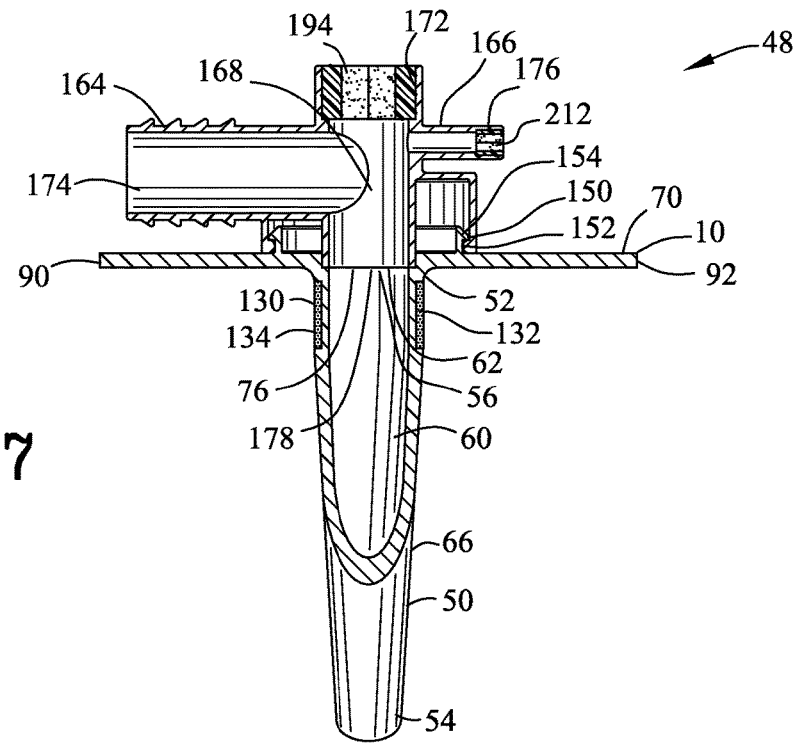
FIG. 7 is a sectional view along line 7-7 in FIG. 3.
Figure 8:
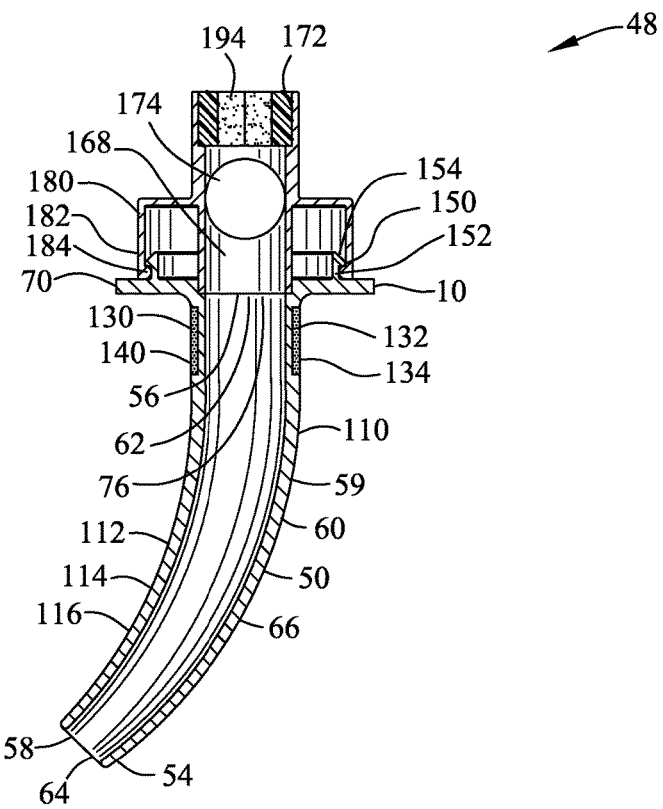
FIG. 8 is a sectional view along line 8-8 in FIG. 3.
Figure 12:
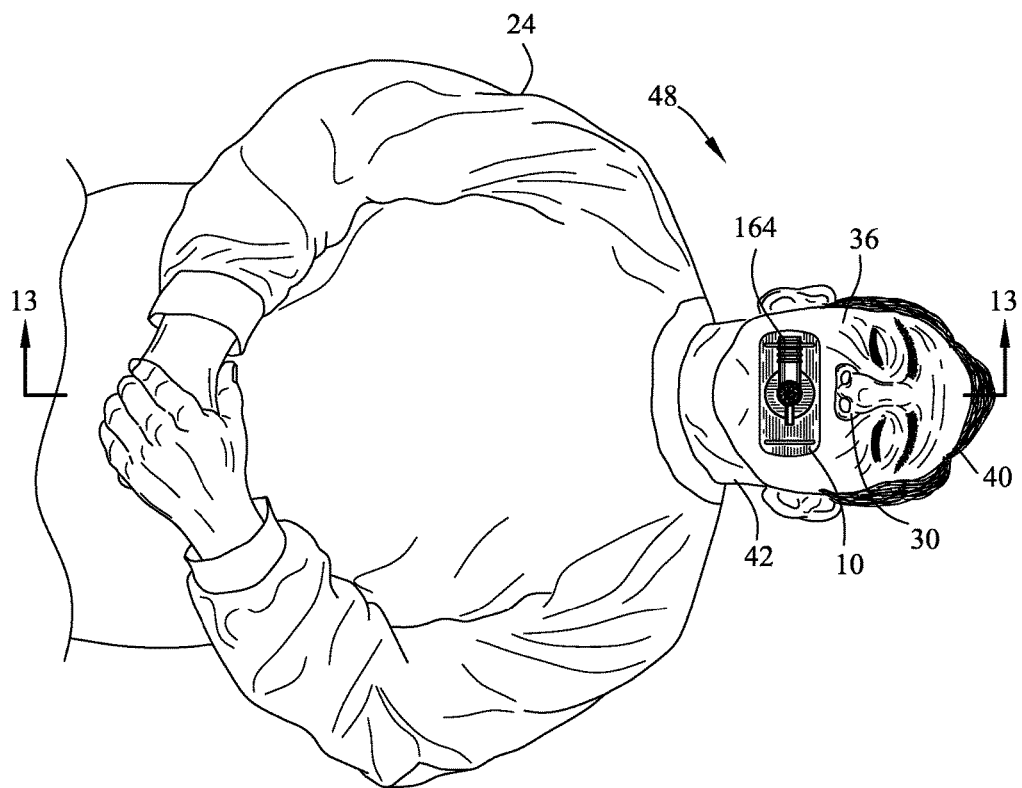
FIG. 12 is a view similar to FIG. 3 illustrating the oropharyngeal device being inserted into the oral cavity of the individual.
Figure 13:
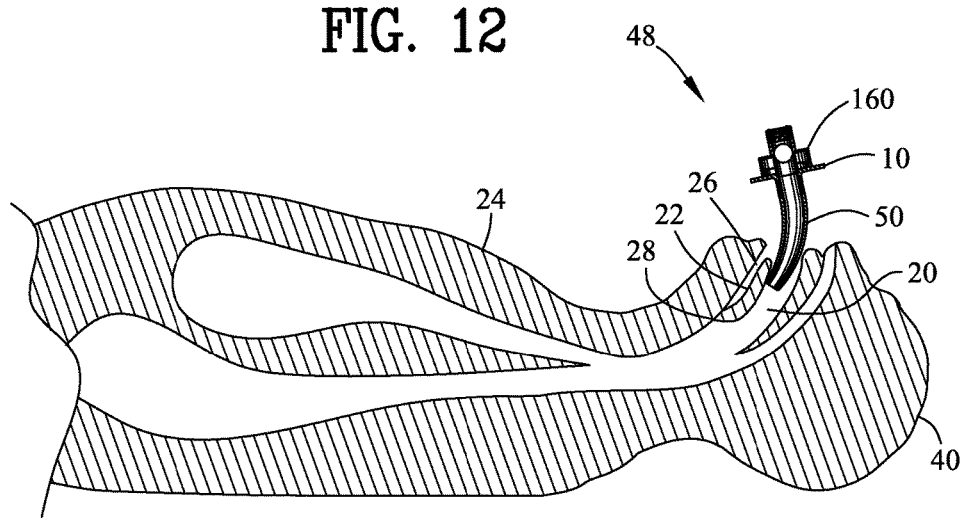
FIG. 13 is a sectional view along line 13-13 in FIG. 12.
Figure 14:
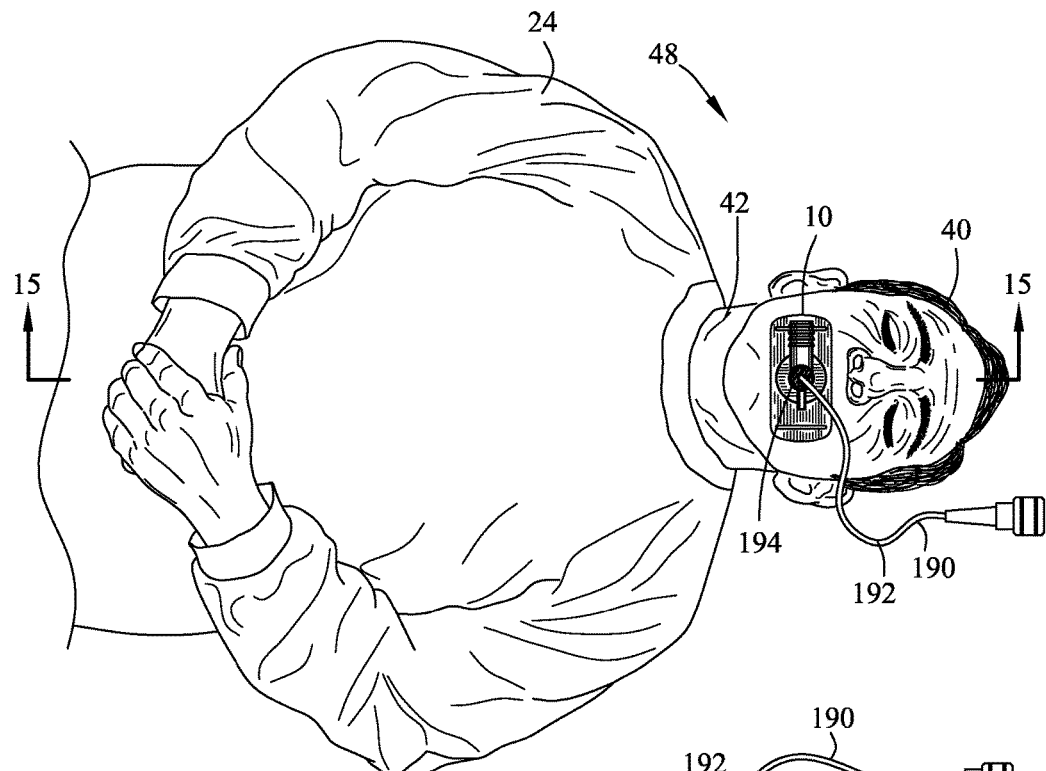
FIG. 14 is a view similar to FIG. 12 illustrating the oropharyngeal device fully inserted into the oral cavity and depressing the tongue of the individual and thereafter an fiber optic device being inserted into the input device aperture.
Figure 15:
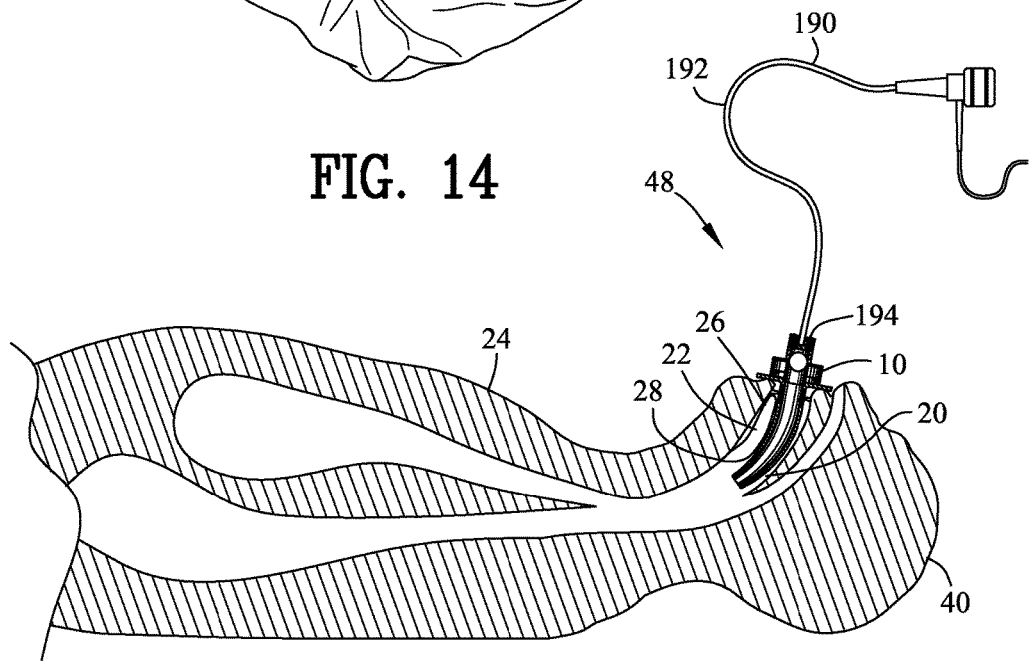
FIG. 15 is a sectional view along line 15-15 in FIG. 14.
Figure 16:
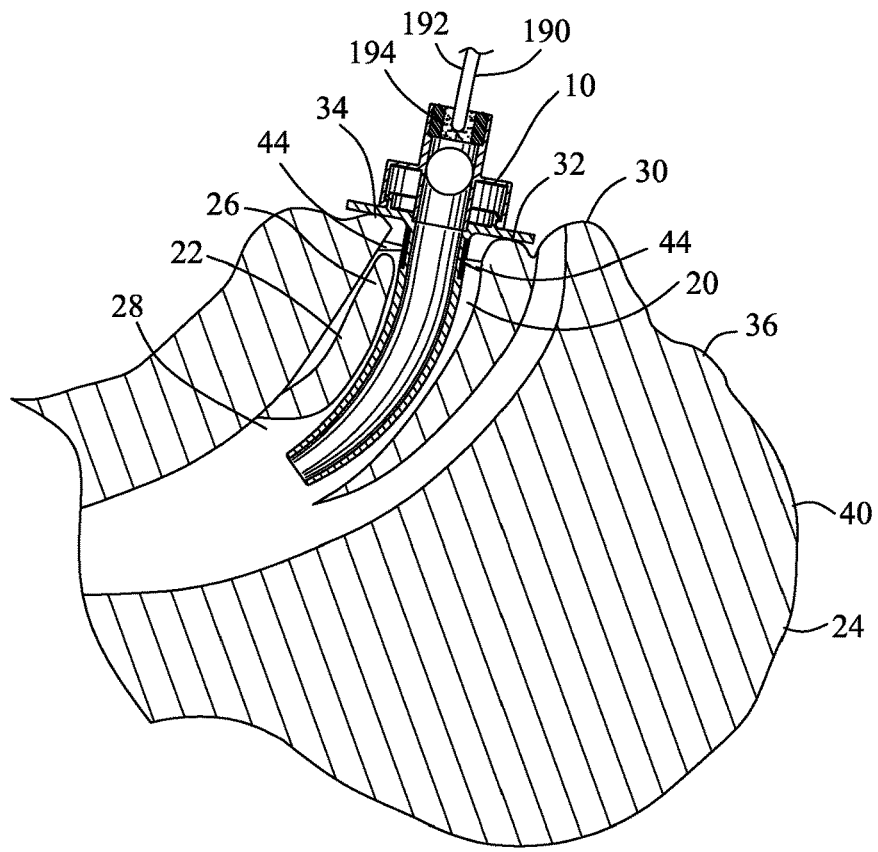
FIG. 16 is an enlarged portion of FIG. 15 illustrating the oropharyngeal device depressing the tongue of the individual and a distal end of a tubular member positioned adjacent to the epiglottis.
Figure 17:
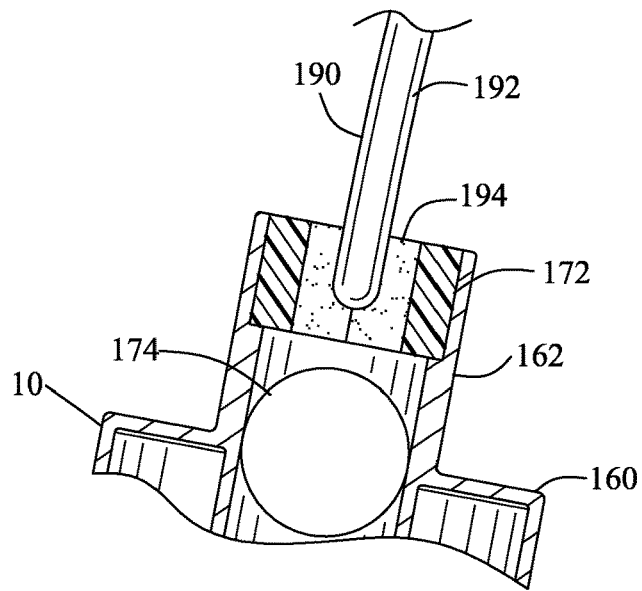
FIG. 17 is an enlarged portion of FIG. 16 illustrating the fiber optic device being inserted into the input device aperture.
Figure 18:
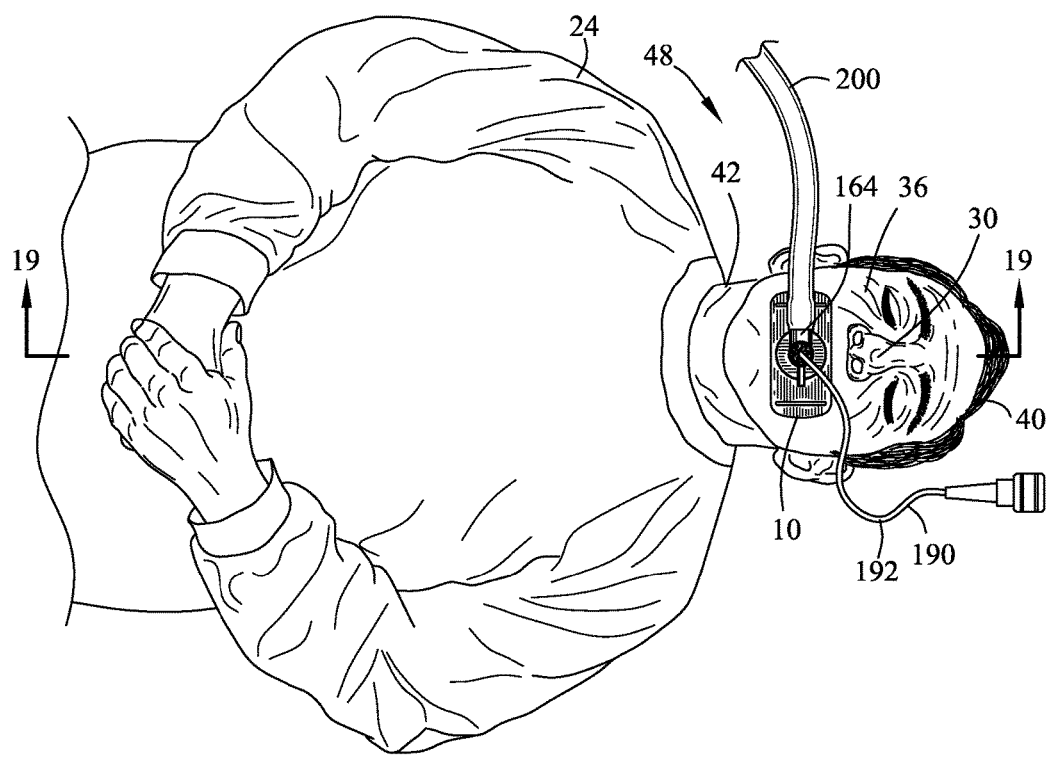
FIG. 18 is a view similar to FIG. 14 illustrating the fiber optic device being fully inserted into the input device aperture for positioning the fiber optic device beyond the epiglottis and with an oxygen conduit coupled with a gaseous cylindrical body.
Figure 19:
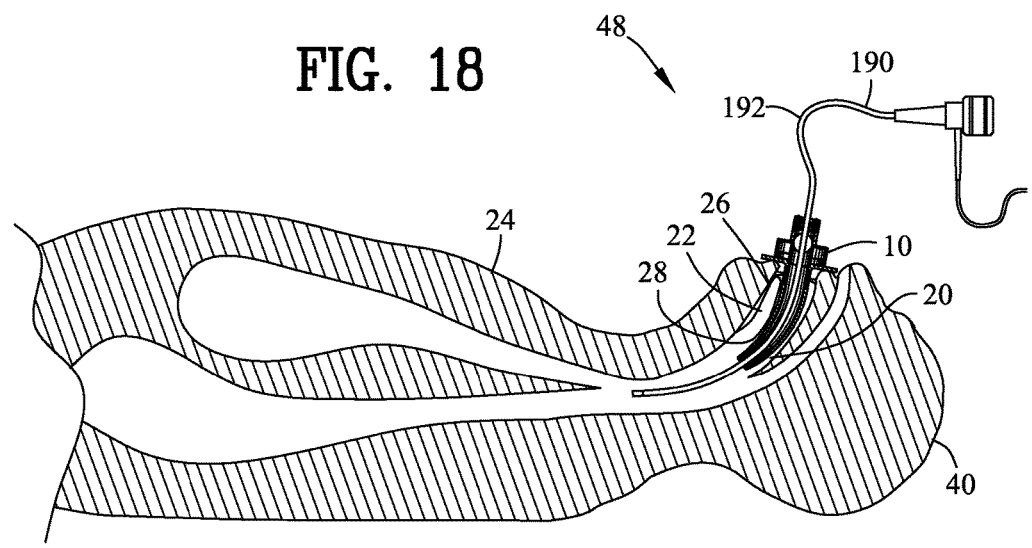
FIG. 19 is a sectional view along line 19-19 in FIG. 18.
Figure 20:
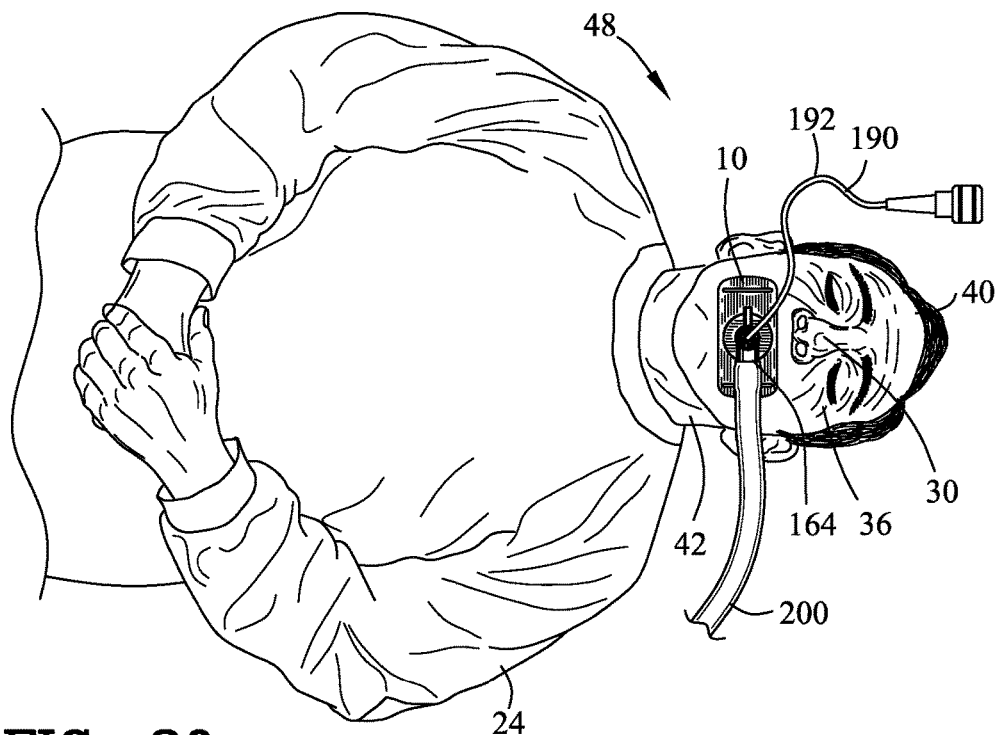
FIG. 20 is a view similar to FIG. 18 illustrating a manifold being rotationally displaced relative to the individual for permitting the oxygen conduit to approach the oropharyngeal device in multiple directions.
Figure 21:
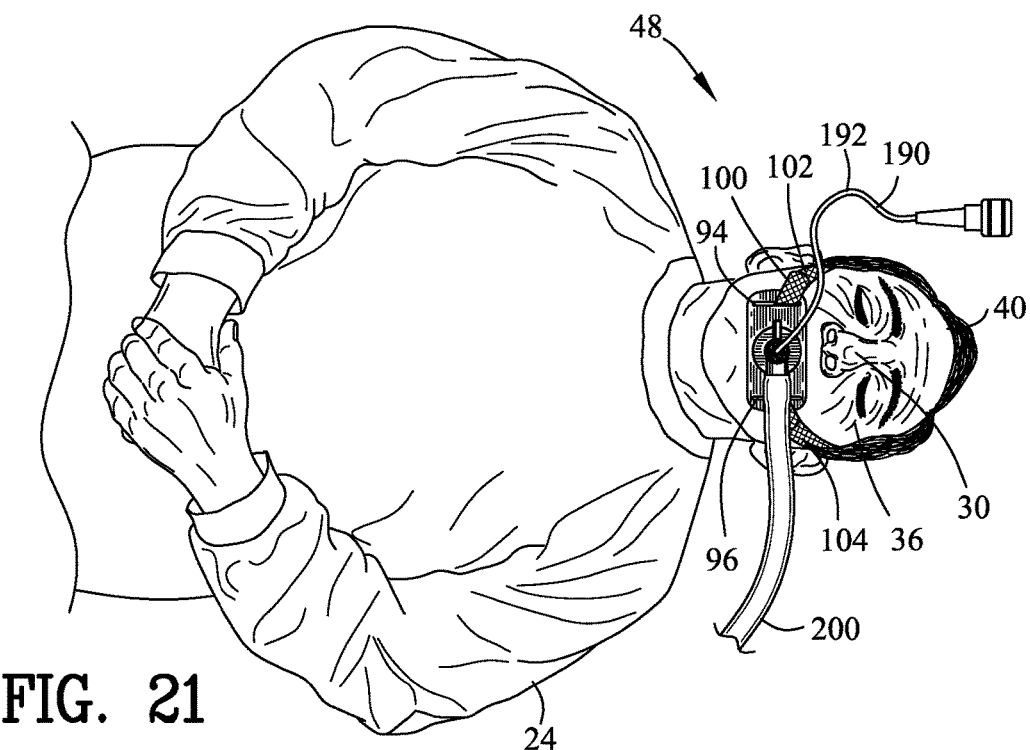
FIG. 21 is a view similar to FIG. 20 illustrating an elastic band engaging a flange for encircling the head or neck of the individual and maintaining oropharyngeal device in the fully inserted position.
Figure 22:
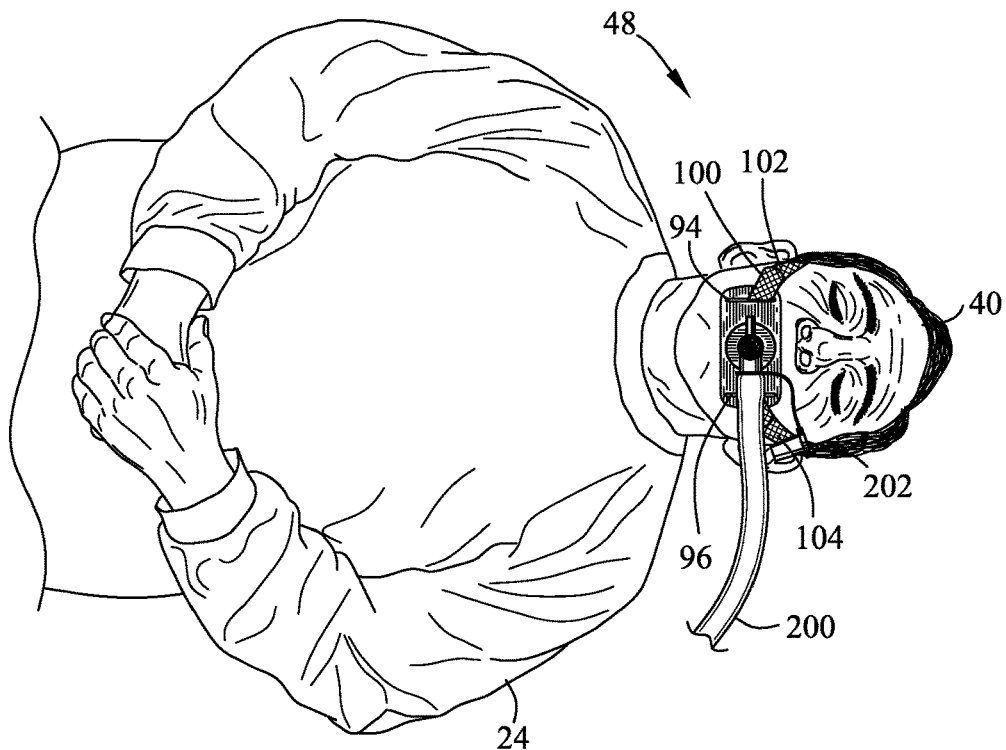
FIG. 22 is a view similar to FIG. 21 illustrating the oropharyngeal device being utilized without the fiber optic device wherein the input device cap engages with an input device aperture.
Figure 23:
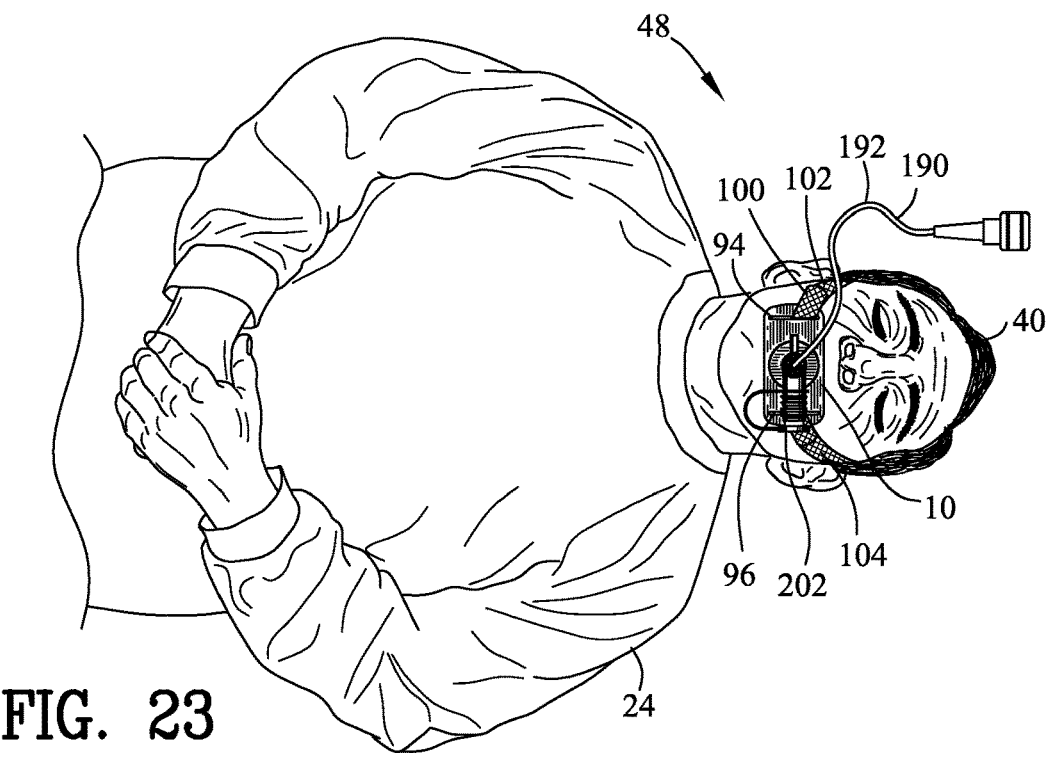
FIG. 23 is a view similar to FIG. 21 illustrating the oropharyngeal device being utilized without the oxygen conduit wherein the gaseous cap engages with a gaseous aperture.
Figure 24:
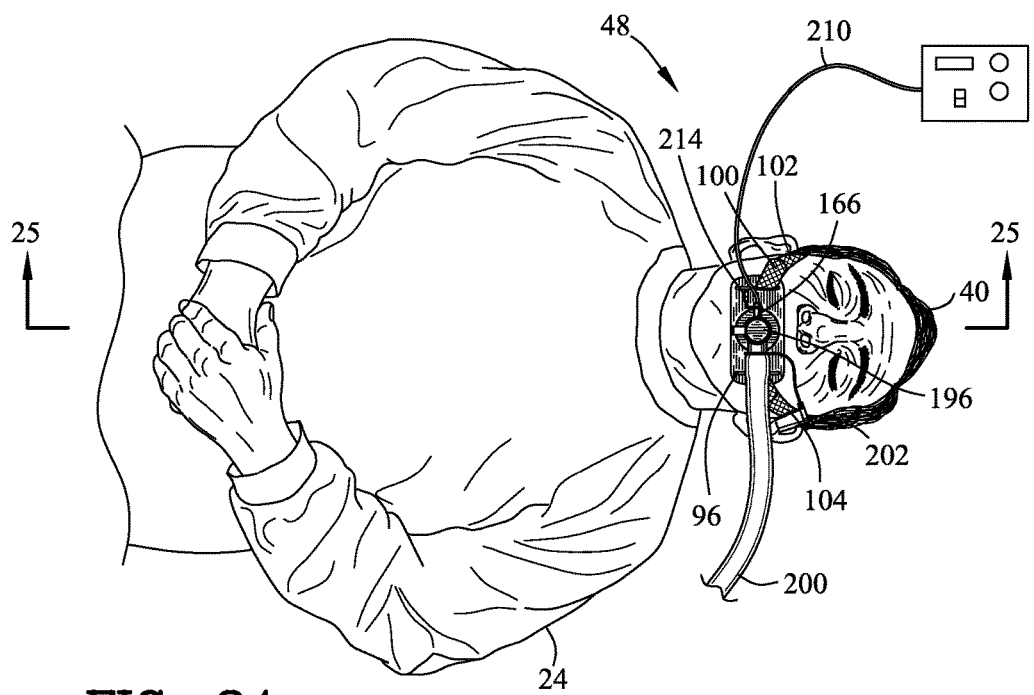
FIG. 24 is a view similar to FIG. 22 illustrating the oropharyngeal device utilizing a carbon dioxide probe being inserted into a carbon dioxide probe aperture.
Figure 25:
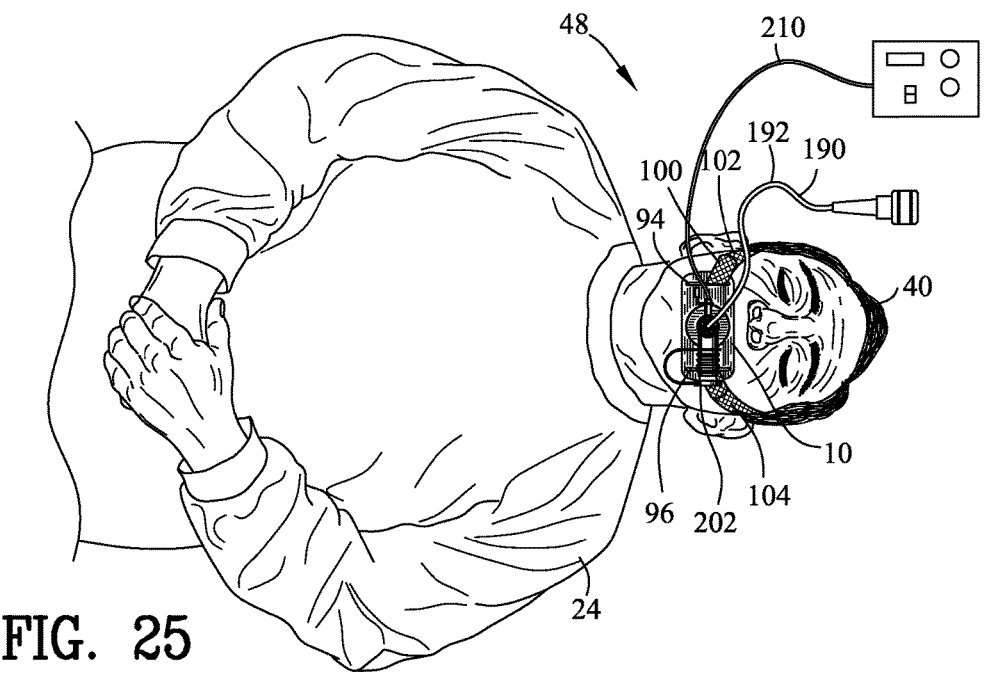
FIG. 25 is a view similar to FIG. 23 illustrating the oropharyngeal device utilizing the carbon dioxide probe being inserted into the carbon dioxide probe aperture.
Figure 26:
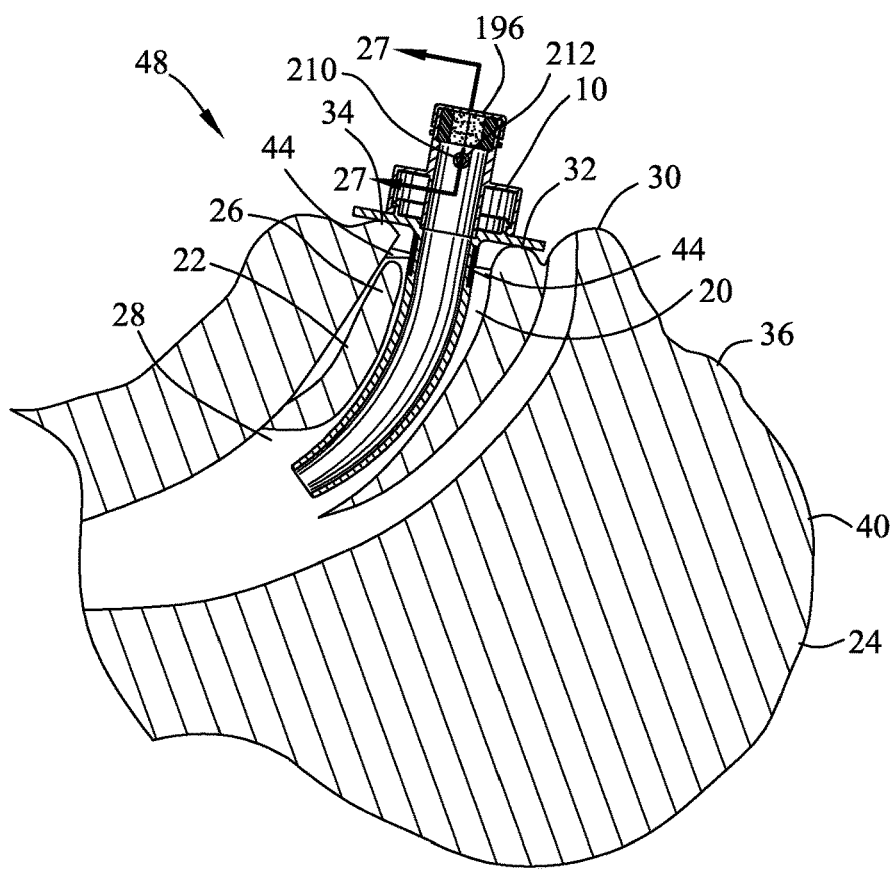
FIG. 26 is a sectional view along line 26-26 in FIG. 24.
Figure 27:
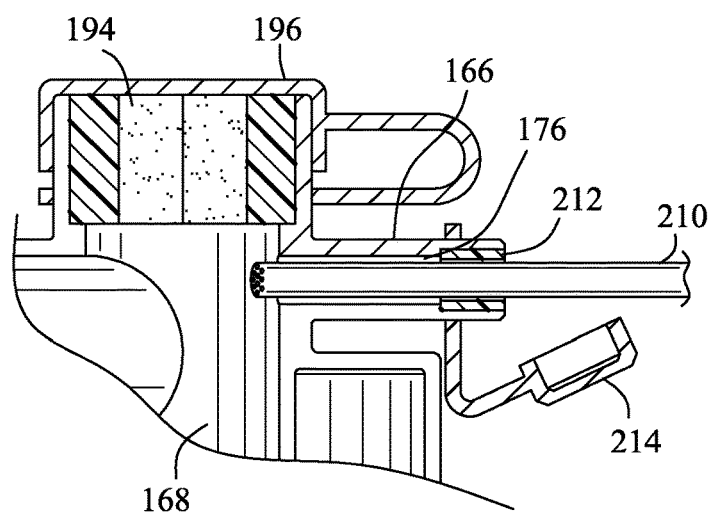
FIG. 27 is a sectional view along line 27-27 in FIG. 26.
Figure 30:
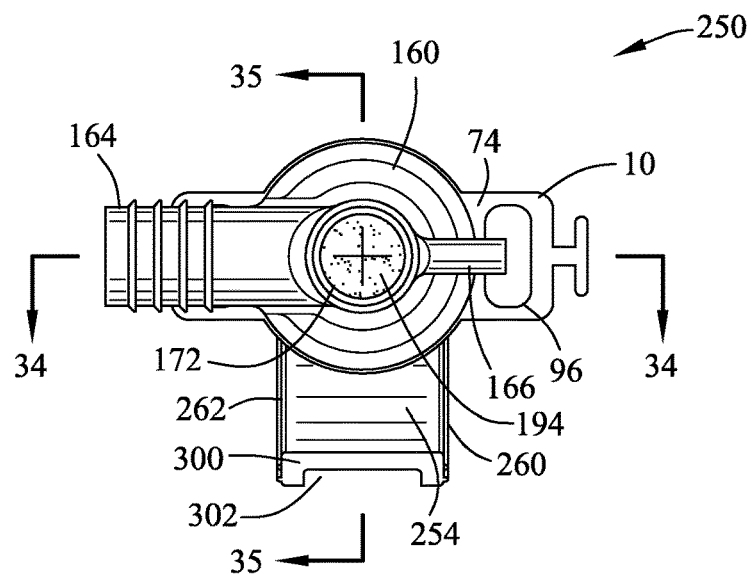
FIG. 30 is a top view of FIG. 28.
Figure 31:
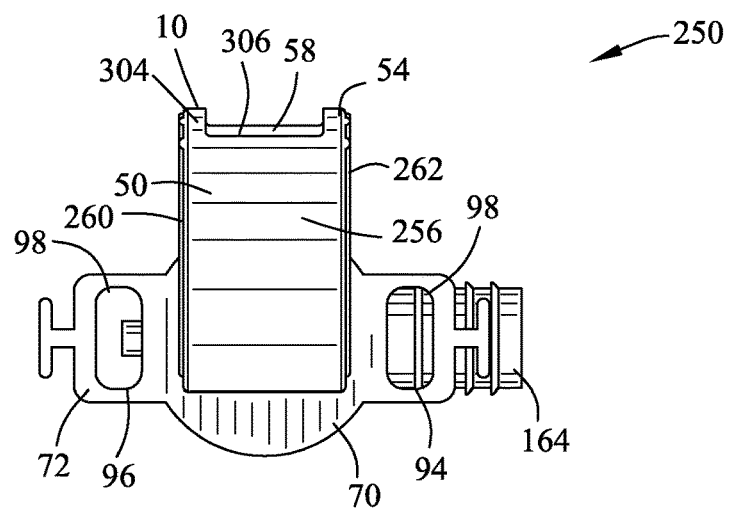
FIG. 31 is a bottom view of FIG. 28.

As best shown in FIGS. 5, 6 and 8, the tubular member 50 defines an arcuate shape 110. More specifically, the tubular member 50 defines a vertical dimension component 112 and a horizontal dimension component 114. The vertical dimension component 112 and the horizontal dimension component 114 may define a three to one ratio 116.

The tubular member 50 may further include an extension tubular member 120. The extension tubular member 120 may be positioned between the proximal end 52 of the tubular member 50 and the flange 70. The extension tubular member 120 defines a constant circumference 122. The constant circumference 122 is equivalent to the first circumference 62 of the primary aperture 56. The extension tubular member 120 is intended to increase the vertical dimension component 112 and the horizontal dimension component 114 for positioning the distal end 54 of the tubular member 50 in a more close proximity to the epiglottis 28.

The tubular member 50 may further include an inset channel 130 positioned adjacent to the proximal end 52 of the tubular member 50. The inset channel 130 has a channel depth 132 and a channel width 134. A deformable annular body 140 has a body thickness 142 and a body width 144. The deformable annular body 140 is positioned within the inset channel 130 for engaging with the teeth 44 of the individual 24. The channel depth 132 and the body thickness 142 are equivalent and the channel width 134 and the body width 144 are equivalent for defining a flush and continuous transition 146 between the tubular member 50 and the deformable annular body 140. The deformable annular body 140 helps distribute the contact area between the teeth 44 of the individual 24 and the tubular member 50 in order to prevent damage to the teeth 44.

As best shown in FIGS. 13, 15, 16, 19 and 26, the gradual narrowing 66 or tapering 68 of the tubular member 50, the circular cross-section 69 and the arcuate shape 110 assist in avoiding a gag reflex of the individual 24 upon insertion of the distal end 54 of the tubular member 50 through the oral cavity 20 and being positioned adjacent to the epiglottis 28. By avoiding a gag reflex the level of sedation may be greatly reduced and thus may reduce the patient stay in the hospital or outpatient facility. Furthermore, the arcuate shape 110 assists in depressing the tongue 26 and maintaining airway patency between the oral cavity 20 and the epiglottis 28.

As shown in FIGS. 14-21, 25 41-53, once the distal end 54 of the tubular member 50 has traversed the oral cavity 20 and is positioned adjacent to the epiglottis 28, an elongated device 190 which may include a fiber optic device 192 may be easily inserted into the input device aperture 172 of the input device cylindrical body 162 for positioned the fiber optic device 190 from the oral cavity 20 to the posterior pharynx at a position right above the vocal cords or the esophagus. The fiber optic device 190 may include bronchoscopy or esophageal gastric examination device. An input device cap 196 may be pivotably coupled to the input device cylindrical body 162 for capping the input device aperture 172.

FIGS. 1-85 illustrate the upper surface 74 of the flange 70 including a circular locking rim 150. The circular locking rim 150 includes a flange cylindrical body 152 extending from the upper surface 74. A flange annular locking body 154 extends from the flange cylindrical body 152.

A manifold 160 includes an input device cylindrical body 162, a gaseous cylindrical body 164, a gaseous measuring cylindrical body 166 and a main cylindrical body 168. The input device cylindrical body 162 defines an input device aperture 172. The gaseous cylindrical body 164 defines a gaseous aperture 174. The gaseous measuring cylindrical body 166 defines a gaseous measuring aperture 176. The main cylindrical body 168 defines an output aperture 178.

The manifold 160 includes a locking cap 180 for engaging with the circular locking rim 150 with the output aperture 178 adjacent to the flange aperture 76. More specifically, the locking cap 180 includes a cap body 182 encircling and extending from the main cylindrical body 168. A manifold annular locking body 184 extends from the cap body 182. The manifold 160 is coupled to the flange 70 by the engagement between the flange annular locking body 154 and manifold annular locking body 184. This engagement between the flange annular locking body 154 and manifold annular locking body 184 permits a rotational displacement of the manifold 160 relative to the flange 70.

A first sphincter valve 194 may be positioned within the input device aperture 172 for permitting the insertion of an elongated device 190 through the tubular member 50 and into the epiglottis 28 and preventing the loss of the source of oxygen supplement.

As shown in FIGS. 18, 20-22, 24, 45 and 50, an oxygen conduit 200 maybe coupled to the gaseous cylindrical body 164 for delivering a flow of oxygen into the tubular member 50 and into the trachea and lungs. Since the engagement between the flange annular locking body 154 and manifold annular locking body 184 permit a rotational displacement of the manifold 160 relative to the flange 70, the oxygen conduit 200 maybe positioned at multiple angles relative to the oropharyngeal device 10. The positioning of the oxygen conduit 200 in various angles may be beneficial by providing improved access to the individual 24 and/or facilitating the coupling to the source of oxygen supplement. The oxygen conduit 200 could be connected to pressured oxygen (PEEP) via an adaptor connected CPAP or BIPAP generator. A gaseous cap 202 may be pivotably coupled to the gaseous cylindrical body 164 for capping the gaseous aperture 174.

As shown in FIGS. 24-27 and 53, a carbon dioxide probe 210 may be easily inserted into the gaseous measuring aperture 176 of the gaseous measuring cylindrical body 166 for positioning the carbon dioxide probe 210 within the manifold 160 for measuring the carbon dioxide level that the individual is exhaling. A measuring cap 214 may be pivotably coupled to the gaseous measuring cylindrical body 166 for capping the gaseous measuring aperture 176.

A second sphincter valve 212 may be positioned within the gaseous measuring aperture 176 for permitting the insertion of the carbon dioxide probe 210 into the manifold 160 and measuring the carbon dioxide level that the individual is exhaling.

The oropharyngeal device 10 is preferably constructed from a hardened plastic. The oropharyngeal device 10 is inserted via oral cavity to maintain airway patency and prevent the tongue from retracing in the upper airway which could occlude larynx and cause respiratory distress. When patients are placed under conscious sedation for procedures like fiber optic bronchoscopy or esophageal gastric examination, loss of upper airway patency could become a problem often leading to use of invasive intubation of trachea and placement on mechanical ventilator support. Conscious sedation is targeted to provide comfort level of sedation and allow faster recovery and discharge of patient on same day of the procedure.

When compared to oral tracheal intubation which may require deeper levels of sedation and prolonged patient stay in the hospital or outpatient facility where procedure and endoscopy is pursued. The oropharyngeal device 10 will allow securing airway patency and connecting via a side channel to a source of oxygen supplement and at the same facilitate direct introduction of a fiber optic device (whether it is a bronchoscopy or an EGD) from the main working channel to the posterior pharynx at a position right above the vocal cords or the esophagus. The oropharyngeal device 10 may be lubricated by a numbing gel to allow topical anesthesia locally and prevent gagging reflex.

The oropharyngeal device 10 could be connected to variable amounts of oxygen flow as required by the patient. Oxygen will be flowing directly to a position so close by epiglottis and vocal cords to allow entry to trachea and lungs. The oropharyngeal device 10 could be connected to pressured oxygen (PEEP) via an adaptor connected CPAP or BIPAP generator.

The oropharyngeal device 10 could be used solely for the purpose of assisting patients in respiratory failure without having to intubate trachea as a simple measure of non-invasive mechanical respiratory support. The oropharyngeal device 10 may be fastened with a broad band of elastic rubber that will attach to insertion holes on both sides of device and wrap around back of patient's head. The oropharyngeal device 10 may have a soft gel area for patient's teeth to prevent clenching of jaws when patient is sedated.

FIGS. 28-53 illustrate a second embodiment 250 of the present invention. The second embodiment 250 is similar to the first embodiment 48, however the second embodiment 250 includes the tubular member 50 having a rectangular cross-section 252 for defining an upper wall 254, a lower wall 256, a primary side wall 260 and a secondary side wall 262. The primary aperture 56 defines a first rectangular area 264 and the secondary aperture 58 defines a second rectangular area 266. The first rectangular area 264 is equal to said second rectangular area 266 for defining a constant rectangular cross-section 268 of the tubular member 50 between the proximal end 52 and the distal end 54 for positioned adjacent to the epiglottis 28.

The arcuate shape 110 of said tubular member 50 defines a vertical dimension component 112 and a horizontal dimension component 114. In the second embodiment 250, the vertical dimension component 112 and the horizontal dimension component 114 define a two to one ratio 270. The tubular member 50 has an intermediate point 280 positioned between the proximal end 52 and the distal end 54. The tubular member 50 includes a linear tubular member 282 extending from the proximal end 52 and the intermediate point 280. The arcuate shape 59 extends from the intermediate point 280 to the distal end 54. The linear tubular member 282 increases the vertical dimension component 112 for positioning the distal end 54 of the tubular member 50 in a more close proximity to the epiglottis 28.

The upper wall 254 includes a first deformable sheet 290 adjacent to the proximal end 52 of the tubular member 50 and the lower wall 256 includes a second deformable sheet 292 adjacent to the proximal end 52 of the tubular member 50 for engaging the teeth 44 of the individual 24.

Figure 32:
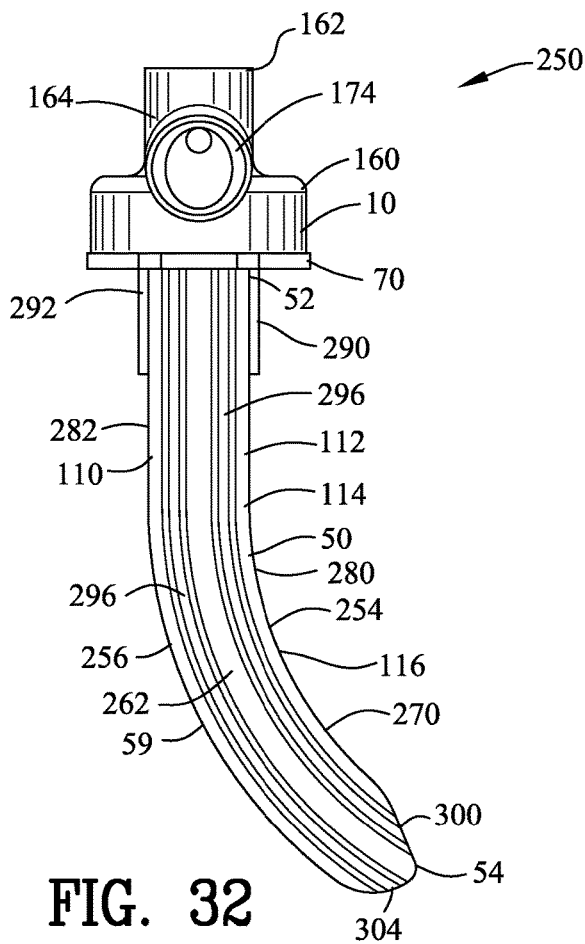
FIG. 32 is a left side view of FIG. 28.
Figure 33:
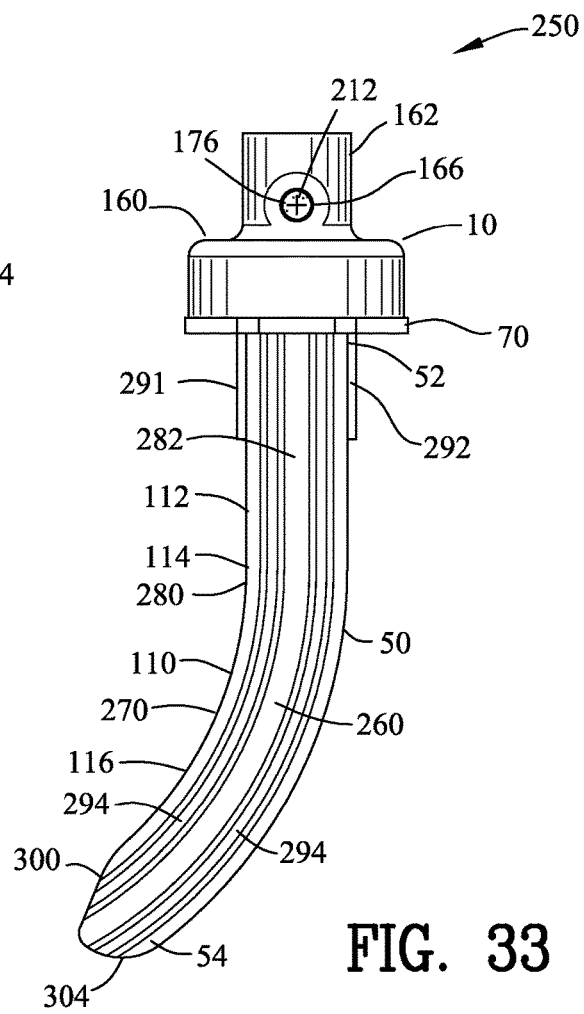
FIG. 33 is a right side view of FIG. 28.
Figure 34:
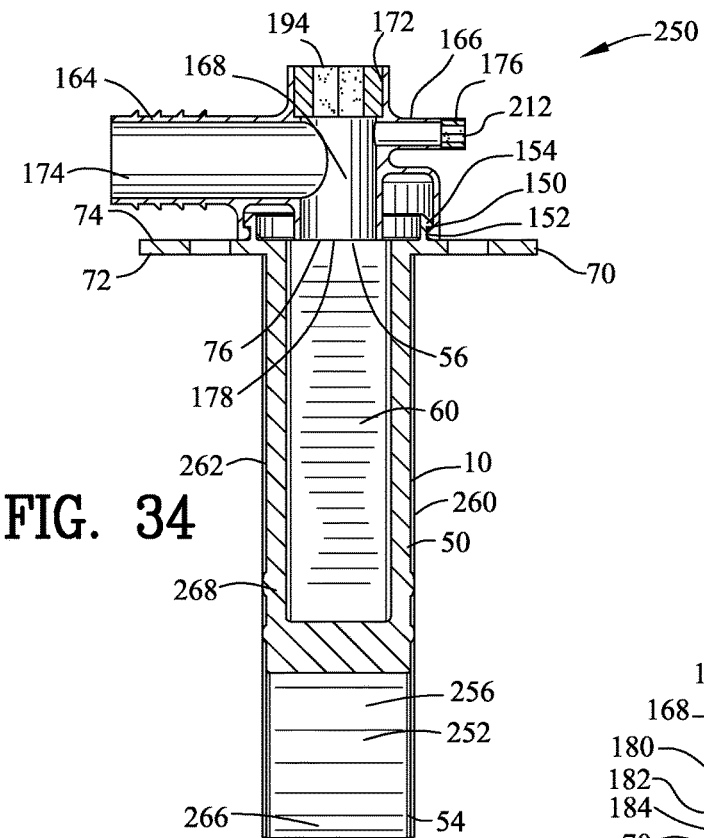
FIG. 34 is a sectional view along line 34-34 in FIG. 30.
Figure 35:
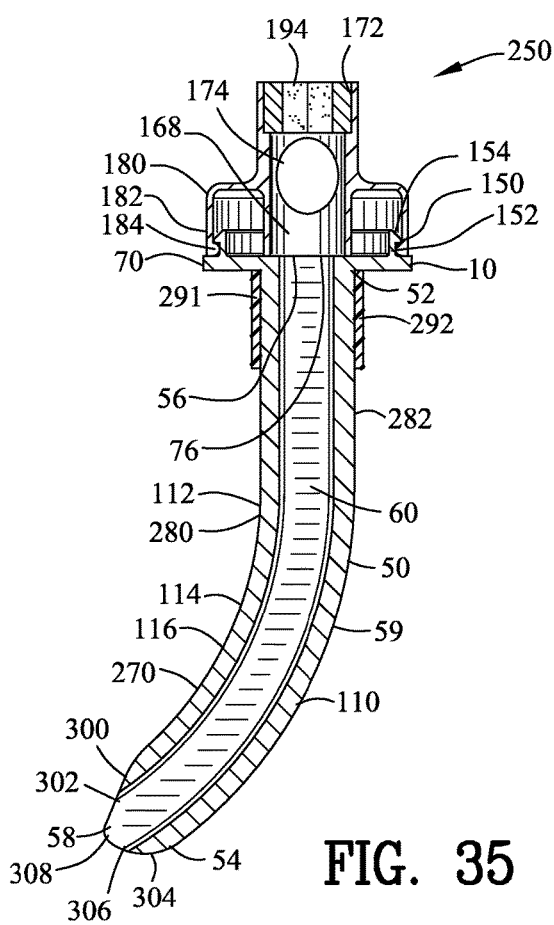
FIG. 35 is a sectional view along line 35-35 in FIG. 30.
Figure 36:
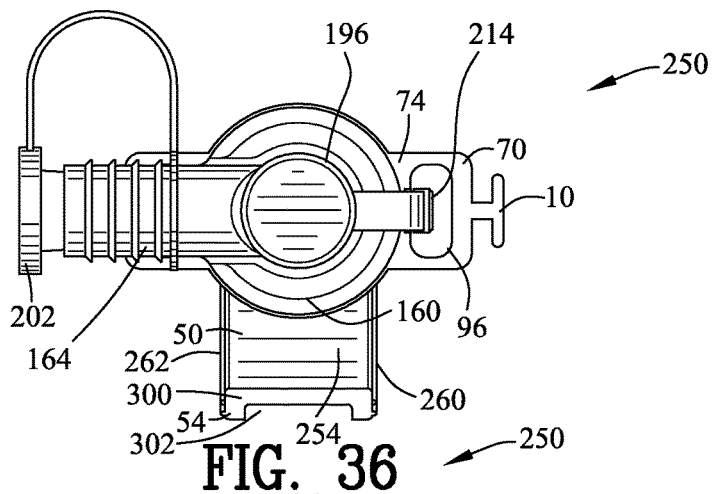
FIG. 36 is a view similar to FIG. 30 illustrating an input device cap engaging with an input device aperture and a gaseous cap engaging with a gaseous aperture.
Figure 37:
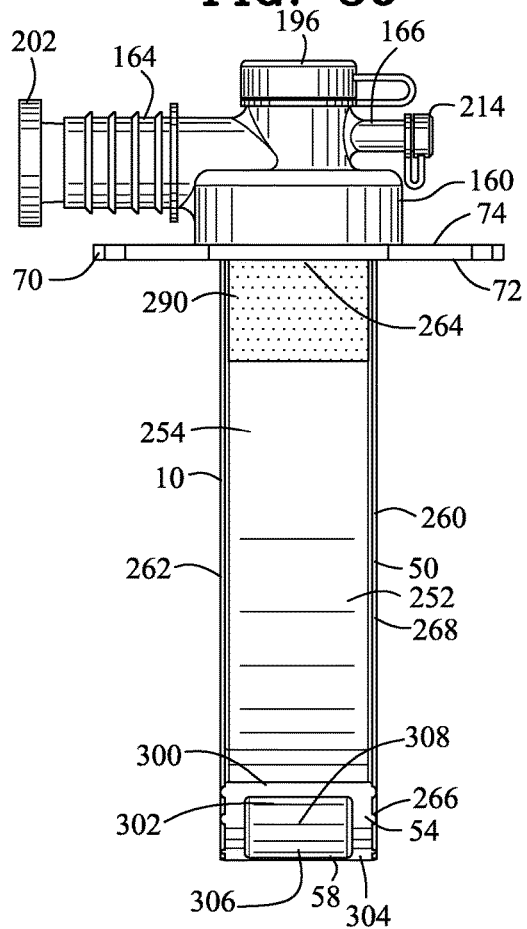
FIG. 37 is a front view of FIG. 36.
Figure 38:
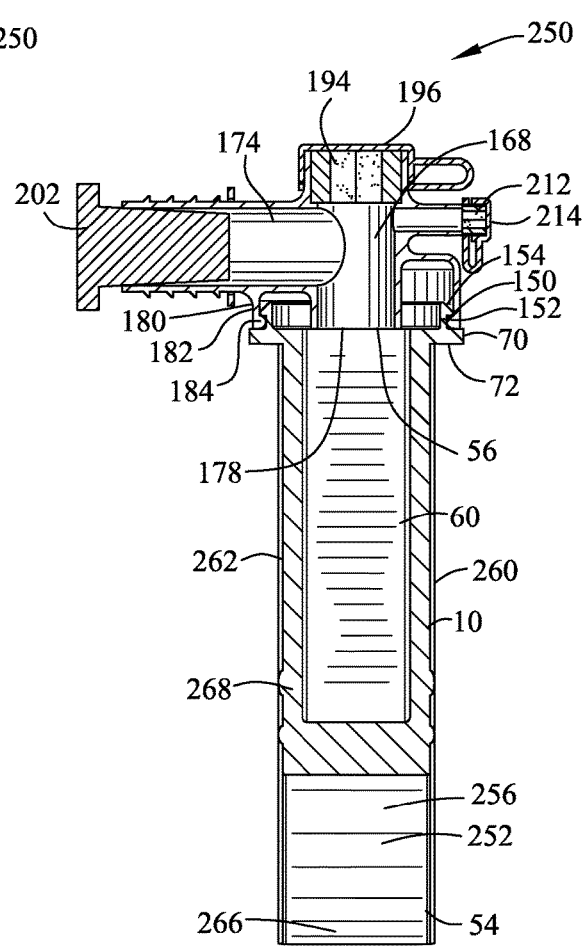
FIG. 38 is a sectional view along line 38-38 in FIG. 36.
Figure 39:
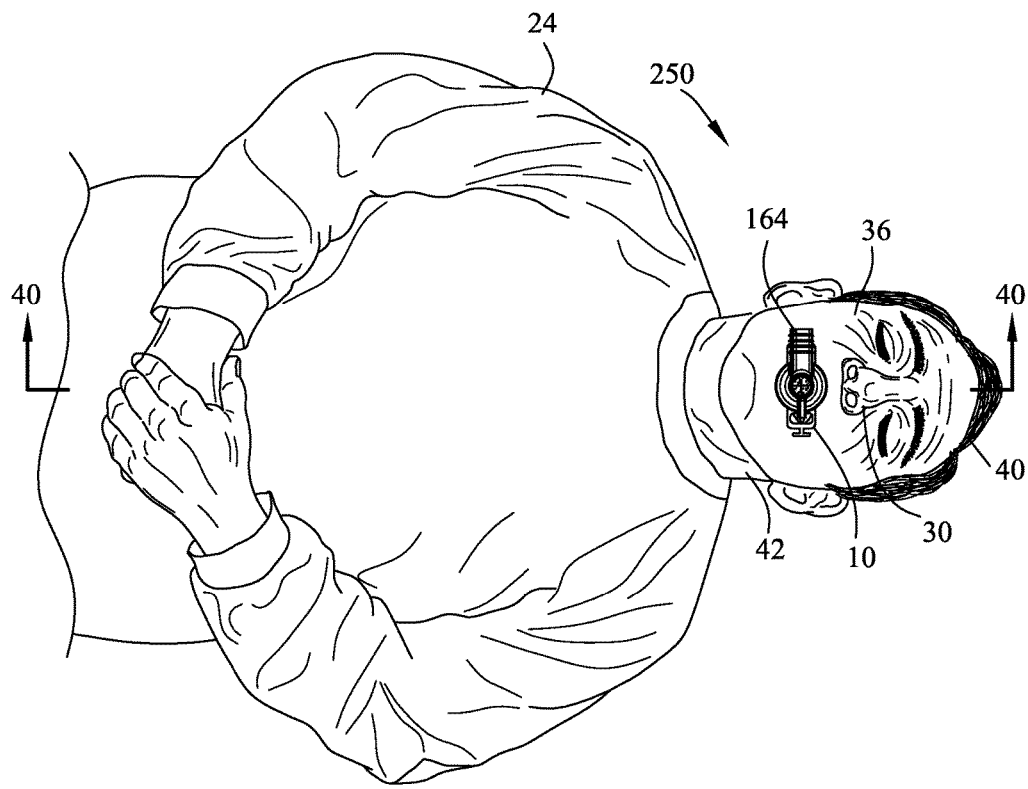
FIG. 39 is a view similar to FIG. 30 illustrating the oropharyngeal device being inserted into the oral cavity of the individual.
Figure 40:
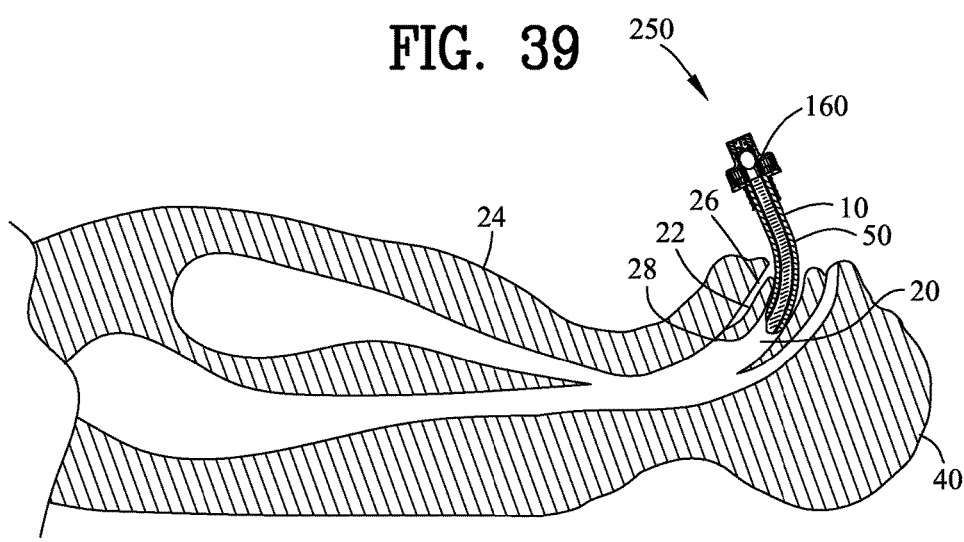
FIG. 40 is a sectional view along line 40-40 in FIG. 39.
Figure 41:
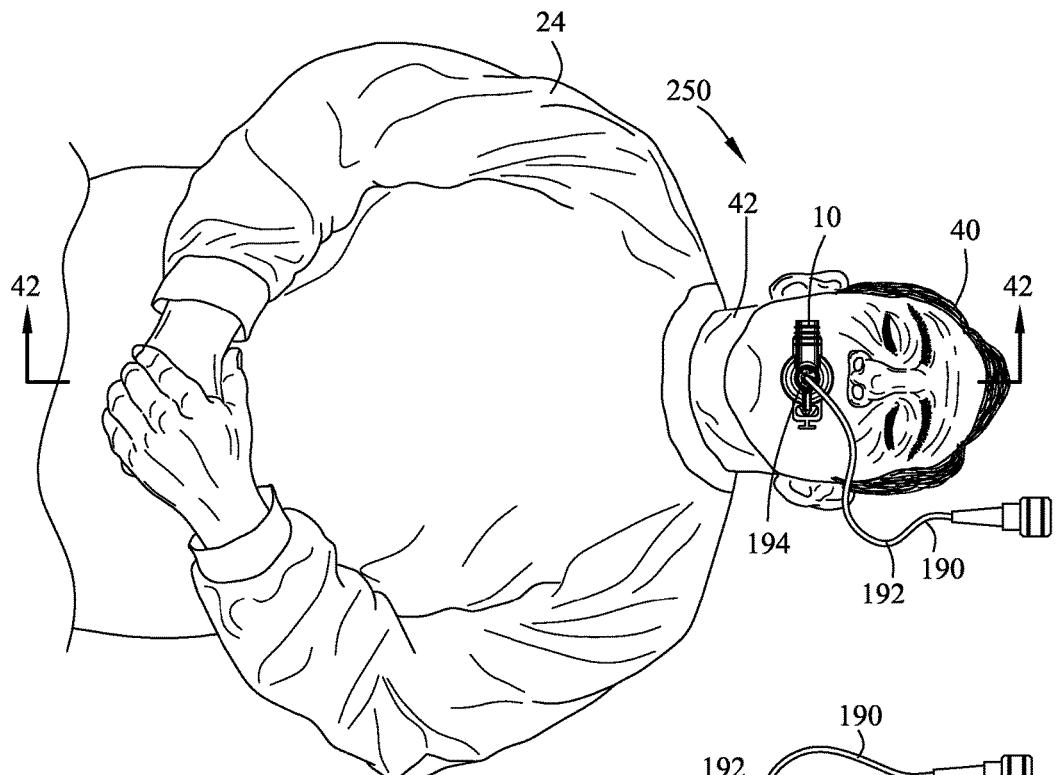
FIG. 41 is a view similar to FIG. 39 illustrating the oropharyngeal device fully inserted into the oral cavity and depressing the tongue of the individual and thereafter an fiber optic device being inserted into the input device aperture.
Figure 42:
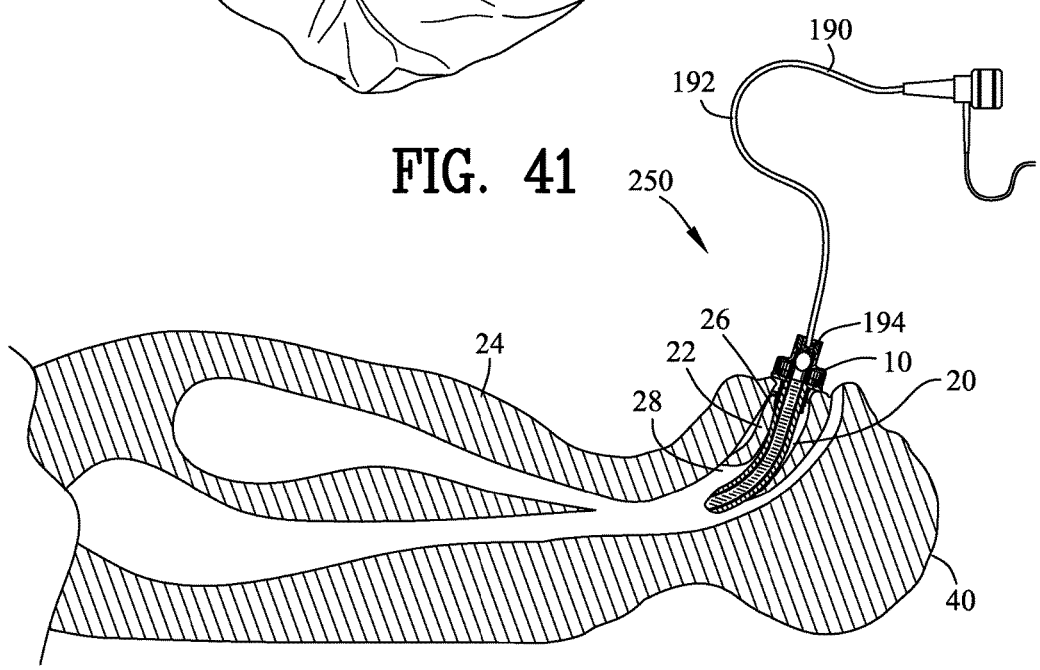
FIG. 42 is a sectional view along line 42-42 in FIG. 41.
Figure 43:
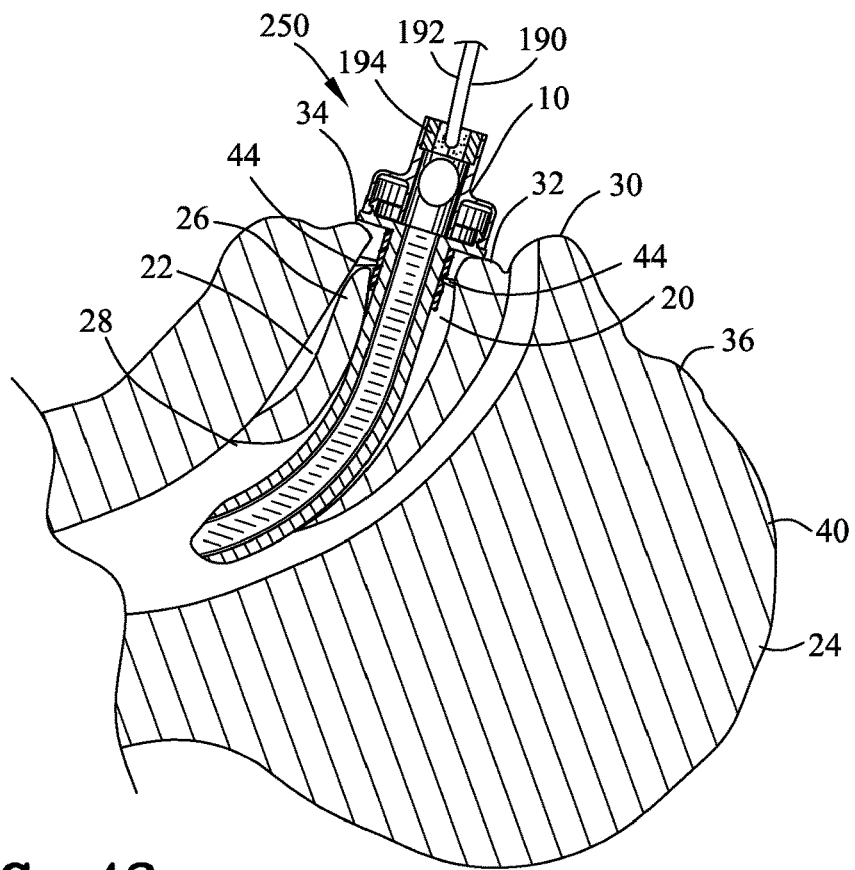
FIG. 43 is an enlarged portion of FIG. 42 illustrating the oropharyngeal device depressing the tongue of the individual and a distal end of a tubular member positioned adjacent to the epiglottis.
Figure 44:
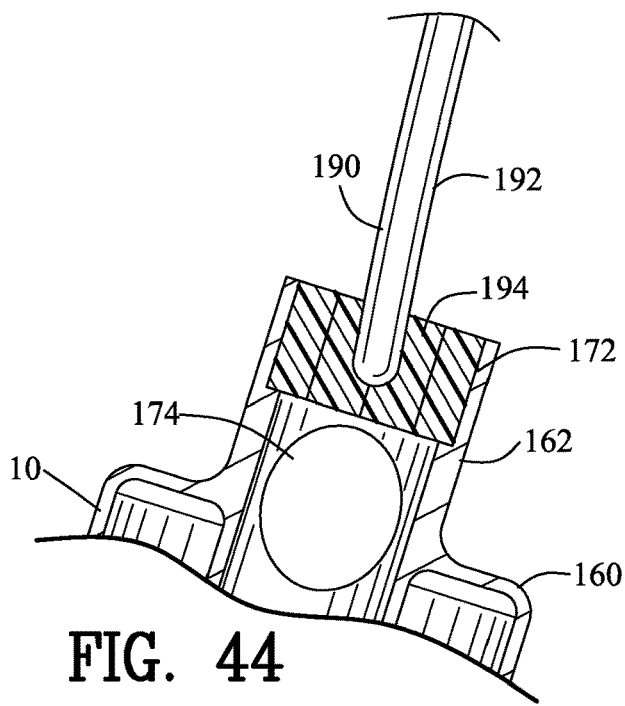
FIG. 44 is an enlarged portion of FIG. 43 illustrating the fiber optic device being inserted into the input device aperture.
Figure 45:
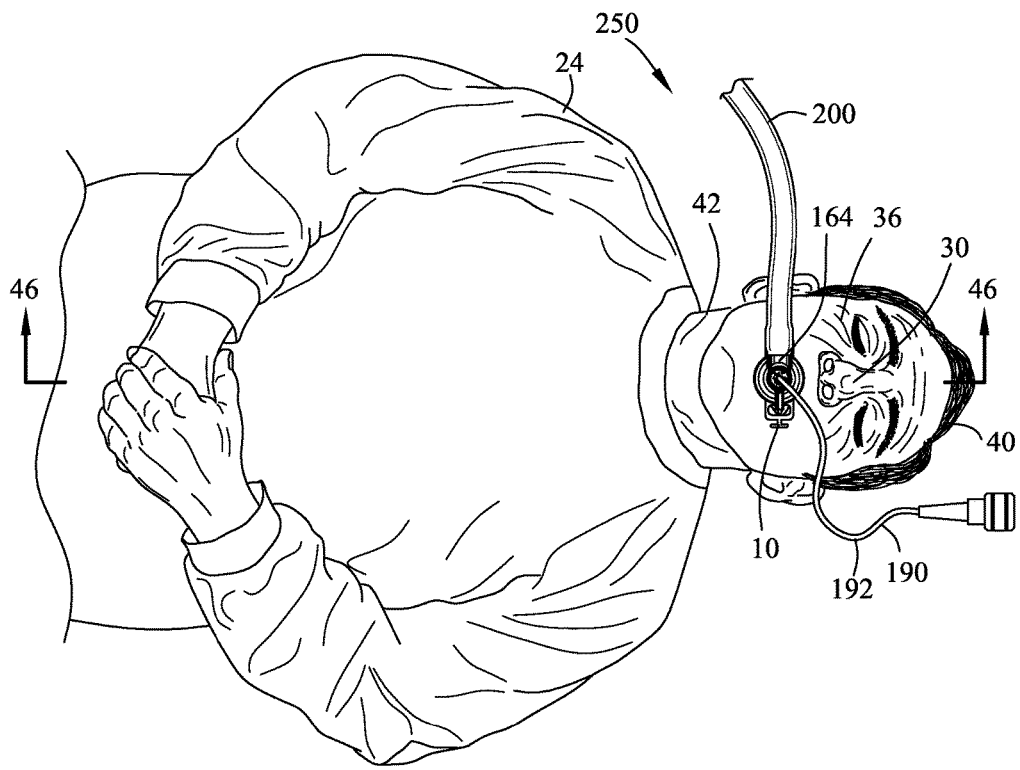
FIG. 45 is a view similar to FIG. 41 illustrating the fiber optic device being fully inserted into the input device aperture for positioning the fiber optic device beyond the epiglottis and with an oxygen conduit coupled with a gaseous cylindrical body.
Figure 46:
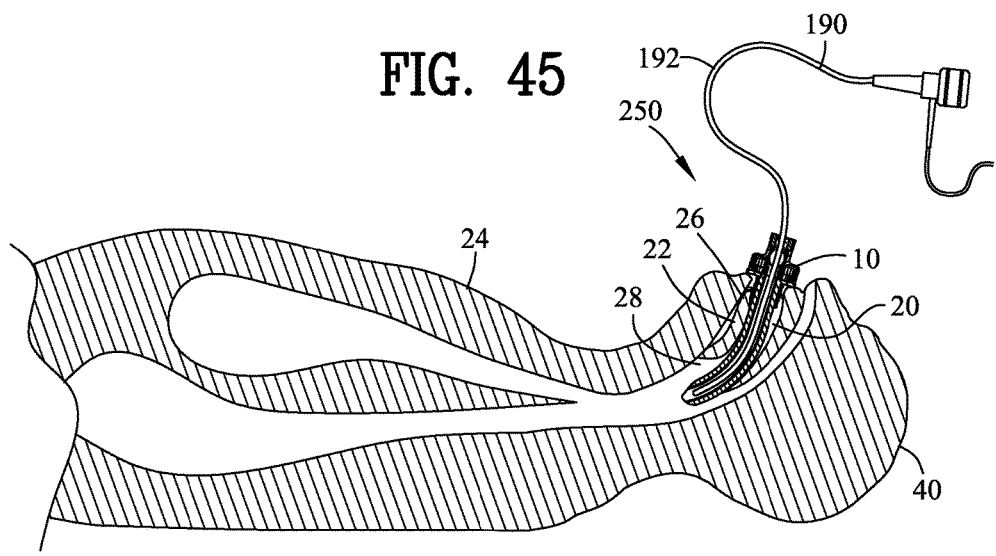
FIG. 46 is a sectional view along line 46-46 in FIG. 45.
Figure 47:
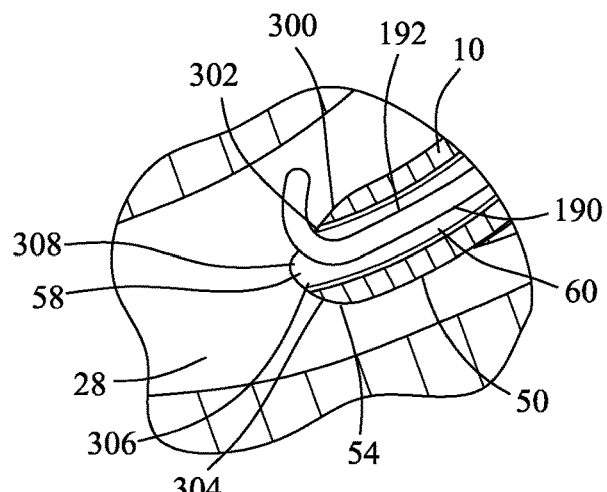
FIG. 47 is an enlarged portion of FIG. 46 illustrating the fiber optic device exiting the oropharyngeal device and thereafter being pivoted in an upper orientation.
Figure 48:
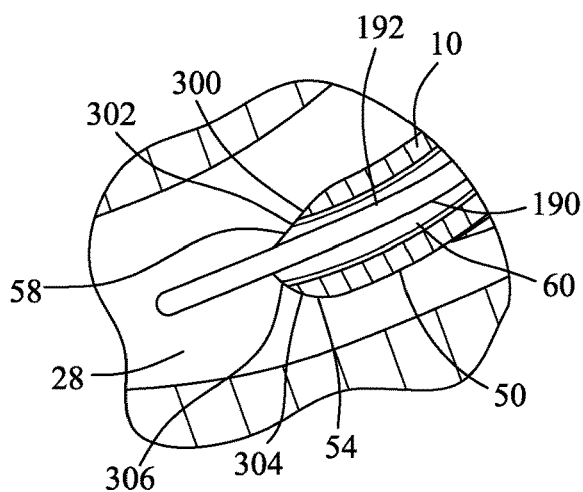
FIG. 48 is an enlarged portion of FIG. 46 illustrating the fiber optic device exiting the oropharyngeal device and thereafter traversing the epiglottis.
Figure 49:
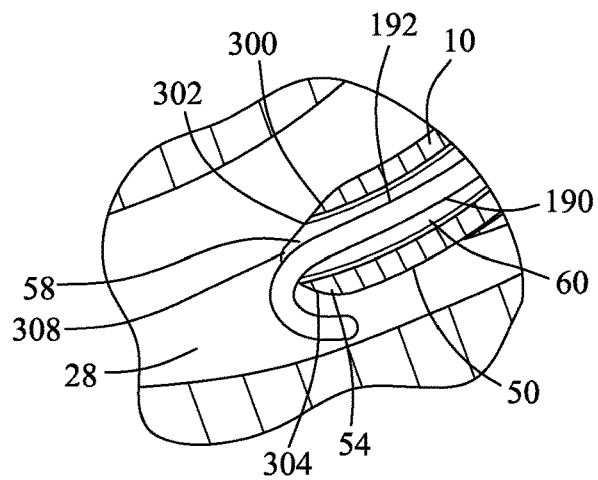
FIG. 49 is an enlarged portion of FIG. 46 illustrating the fiber optic device exiting the oropharyngeal device and thereafter being pivoted in a lower orientation.
Figure 50:
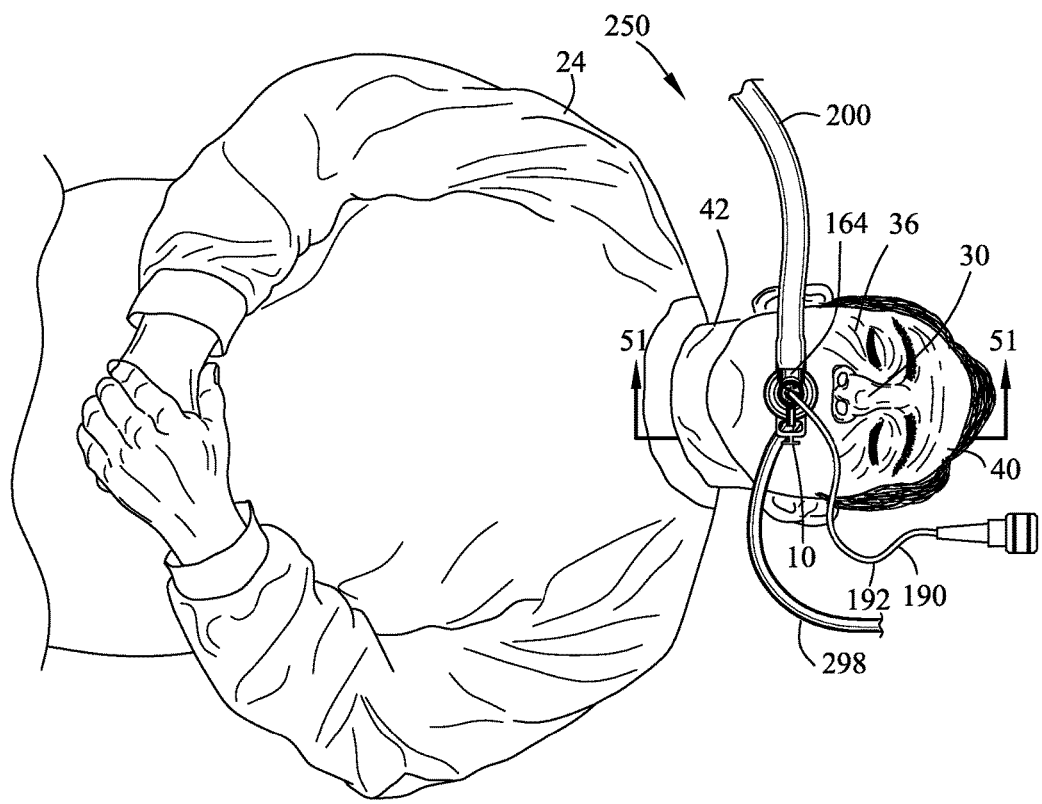
FIG. 50 is a similar view to FIG. 45 illustrating a saliva suction hose being positioned adjacent to the oropharyngeal device.
Figure 51:
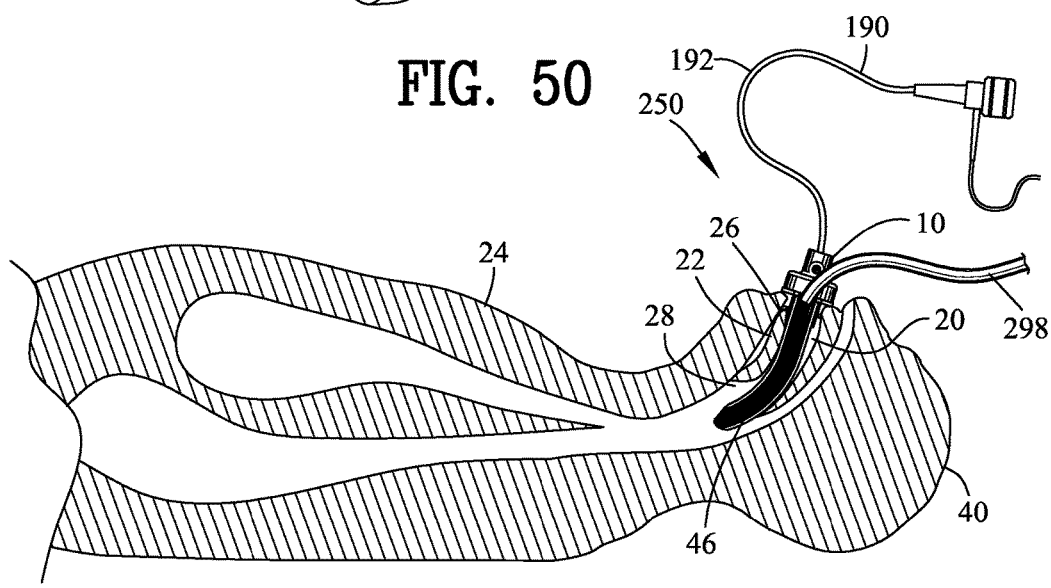
FIG. 51 is a sectional view along line 51-51 in FIG. 50.
Figure 52:
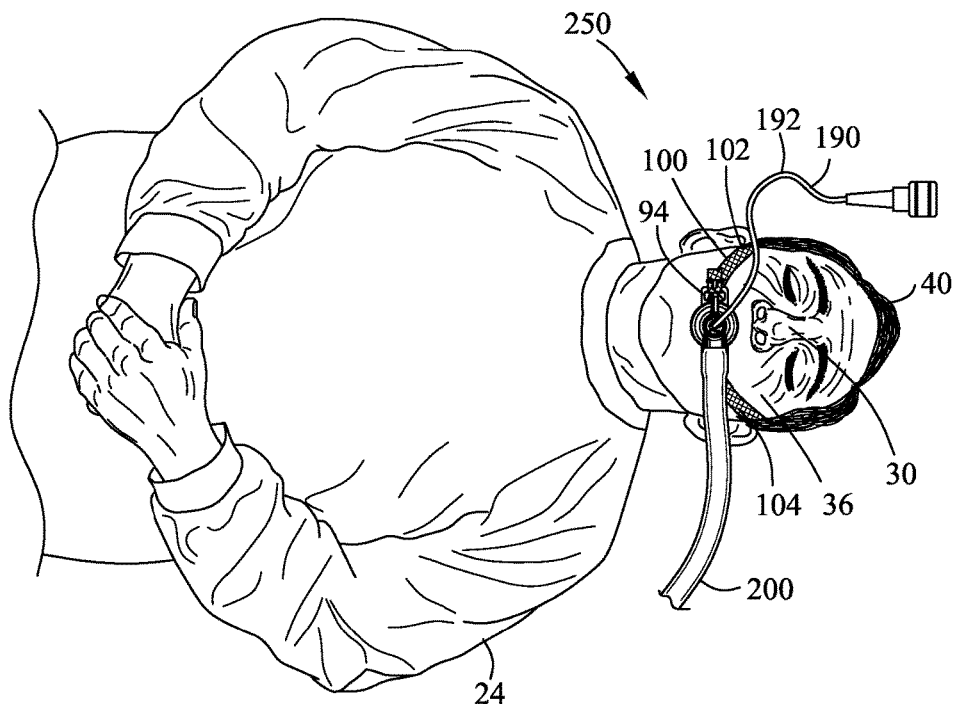
FIG. 52 is a view similar to FIG. 45 illustrating a manifold being rotationally displaced relative to the individual for permitting the oxygen conduit to approach the oropharyngeal device in multiple directions and an elastic band engaging a flange for encircling the head or neck of the individual and maintaining oropharyngeal device in the fully inserted position.
Figure 53:
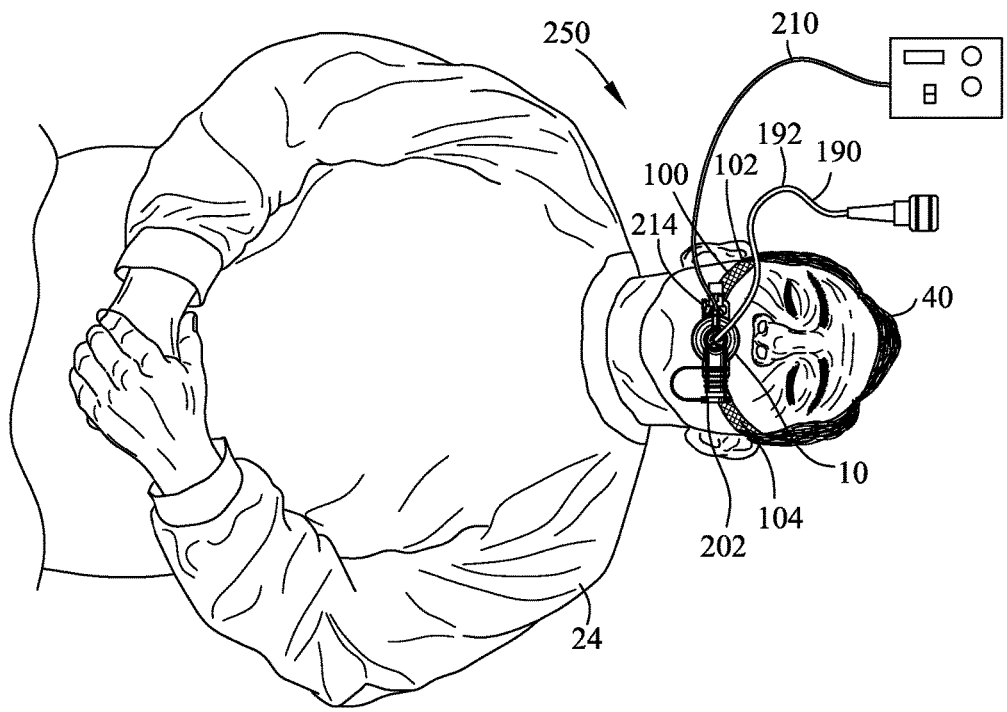
FIG. 53 is a view similar to FIG. 52 illustrating the oropharyngeal device utilizing the carbon dioxide probe being inserted into the carbon dioxide probe aperture.
Figure 56:
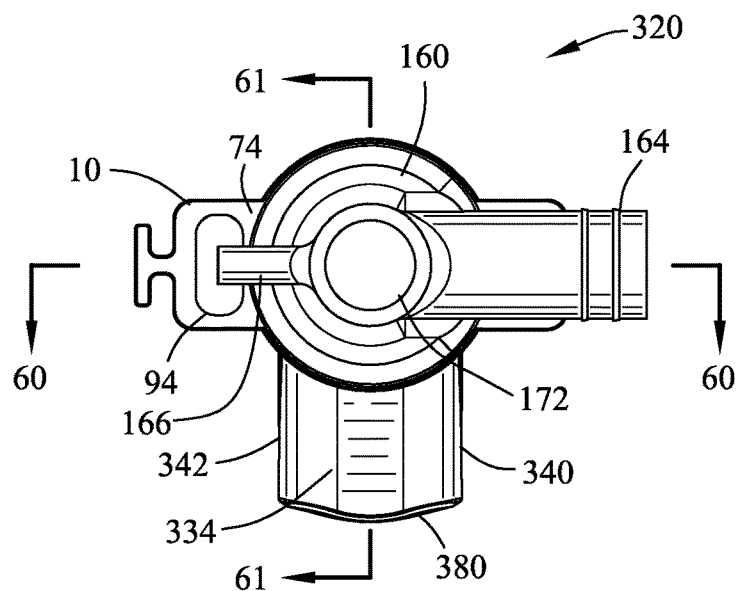
FIG. 56 is a top view of FIG. 54.
Figure 57:
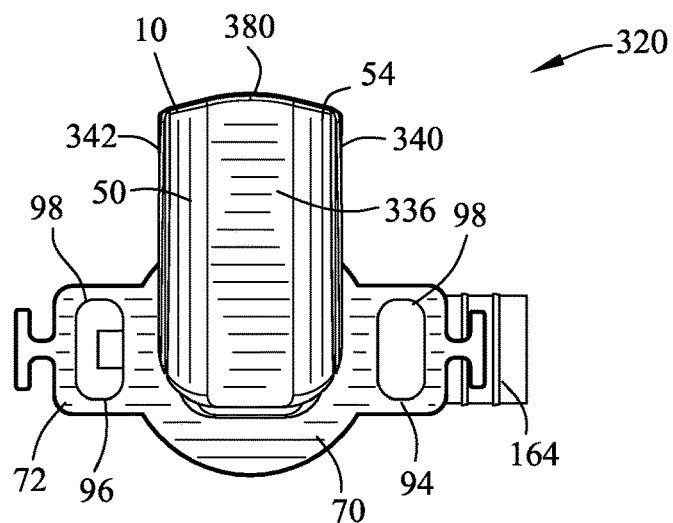
FIG. 57 is a bottom view of FIG. 54.
Figures 60, 61:
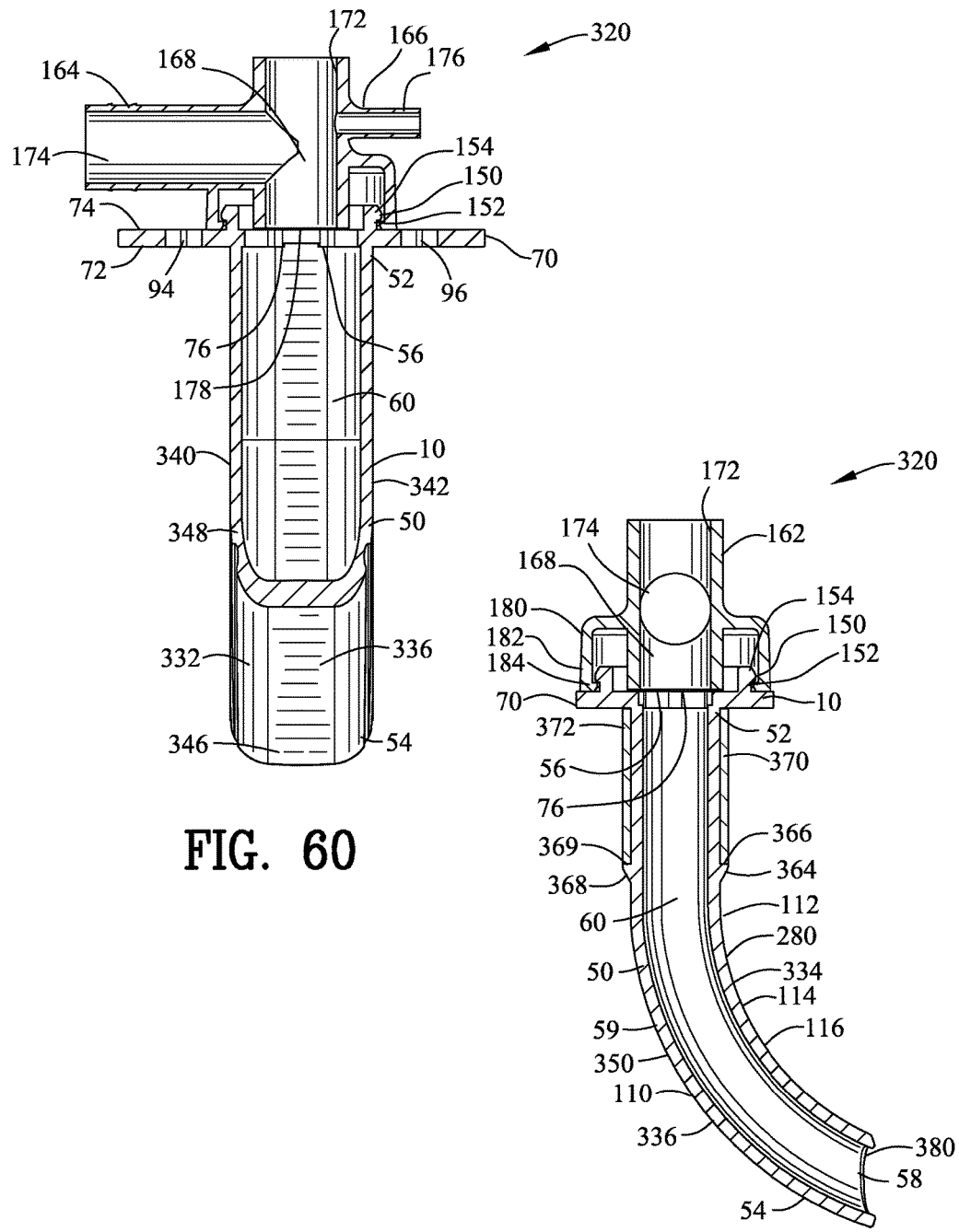
FIG. 60 is a sectional view along line 60-60 in FIG. 56.
FIG. 61 is a sectional view along line 61-61 in FIG. 56.
Figure 62:
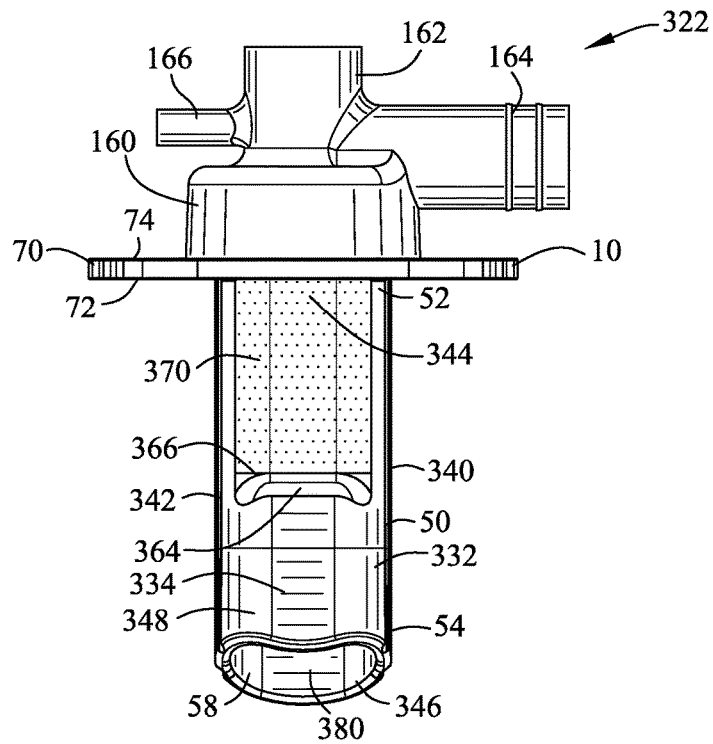
FIG. 62 is a front view of a fourth embodiment of the oropharyngeal device of the present invention.
Figure 63:
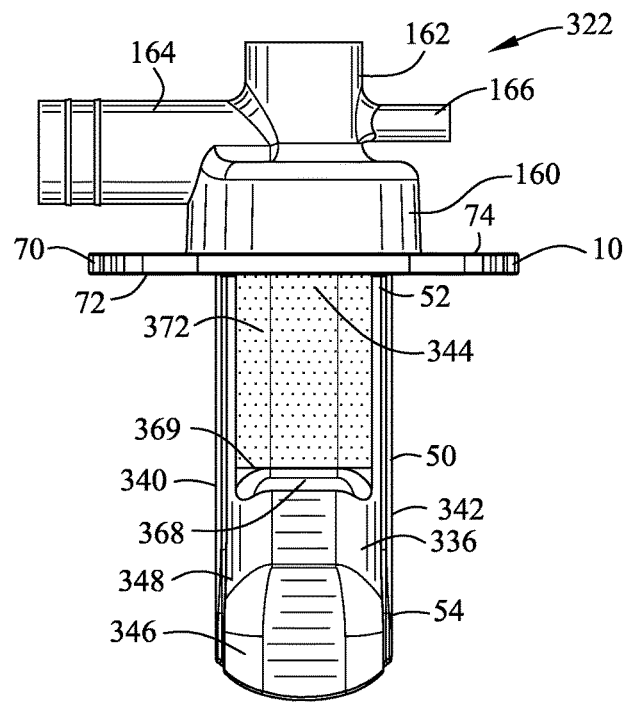
FIG. 63 is a rear view of FIG. 62.
Figure 64:
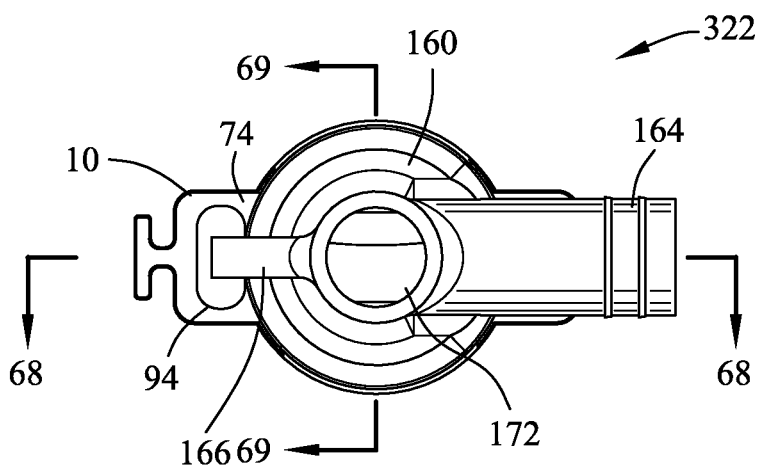
FIG. 64 is a top view of FIG. 62.
Figure 65:
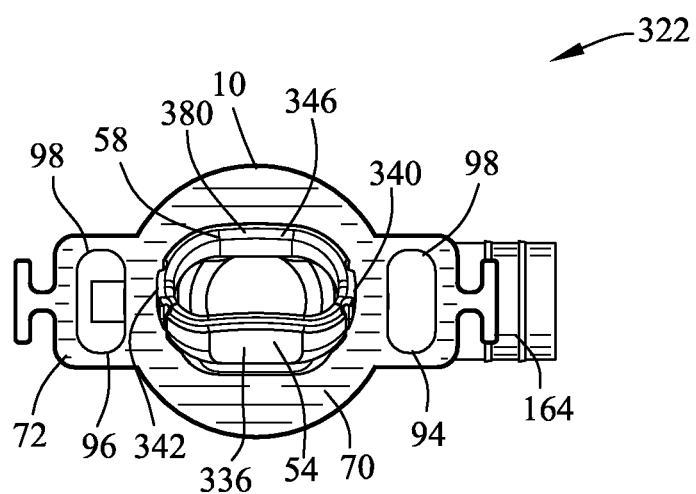
FIG. 65 is a bottom view of FIG. 62.
Figure 66:
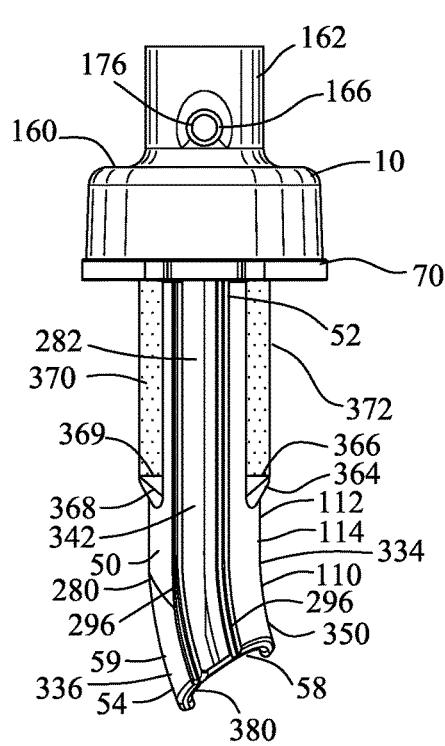
FIG. 66 is a left side view of FIG. 62.
Figure 67:
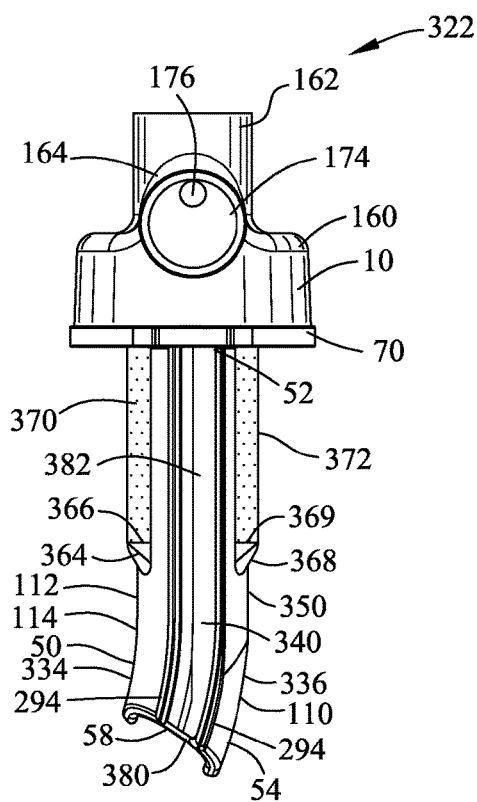
FIG. 67 is a right side view of FIG. 62.
Figure 68:
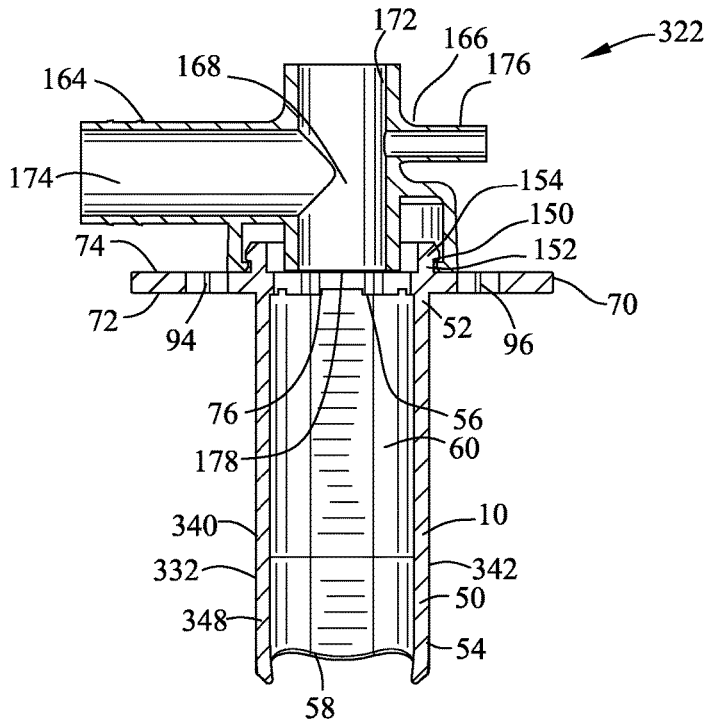
FIG. 68 is a sectional view along line 68-68 in FIG. 64.
Figure 69:
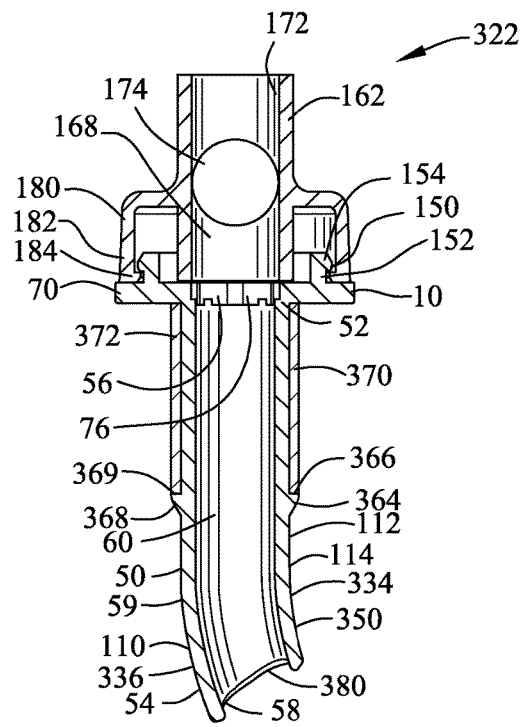
FIG. 69 is a sectional view along line 69-69 in FIG. 64.
Figure 72:
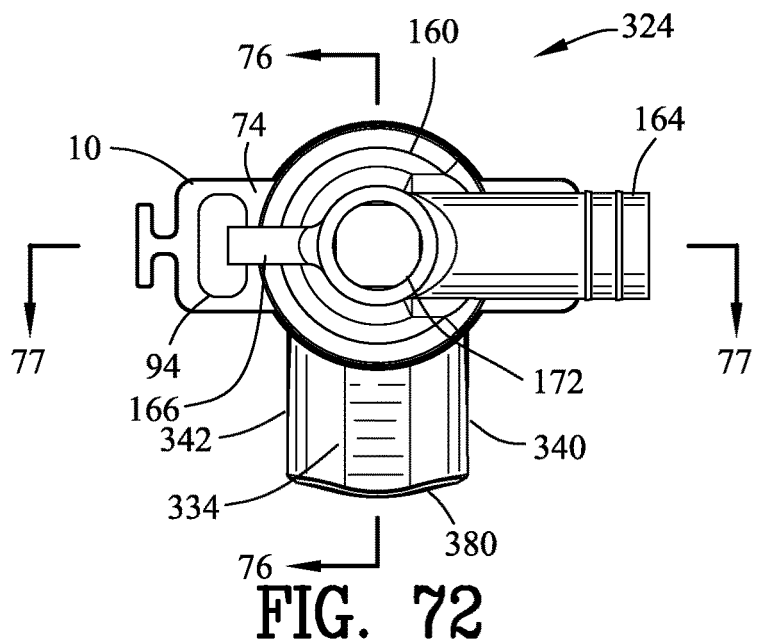
FIG. 72 is a top view of FIG. 70.
Figure 73:
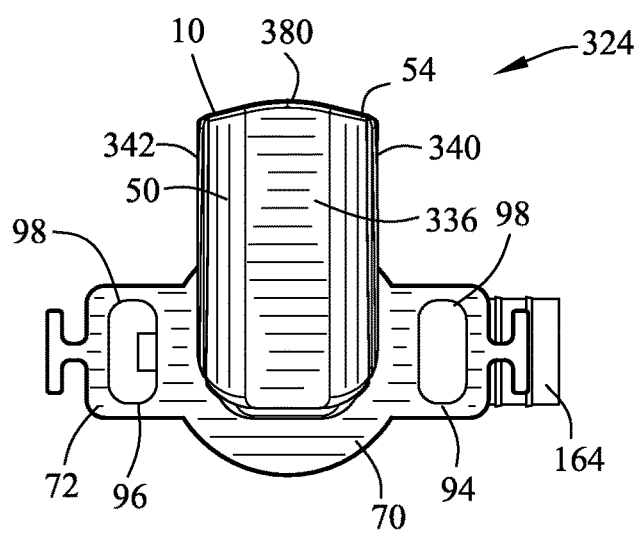
FIG. 73 is a bottom view of FIG. 70.
Figures 76, 77:
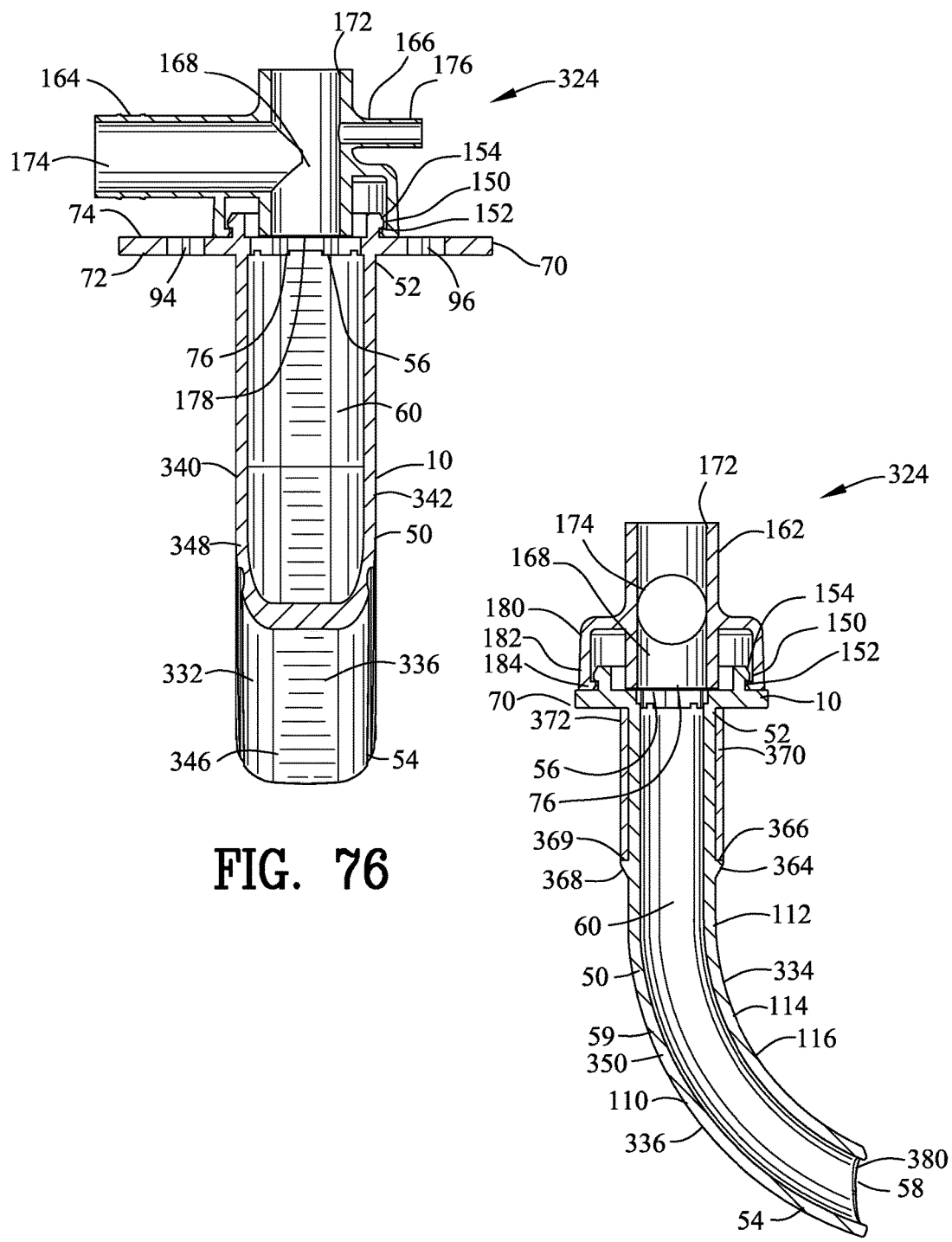
FIG. 76 is a sectional view along line 76-76 in FIG. 72.
FIG. 77 is a sectional view along line 77-77 in FIG. 72.
Figure 78:
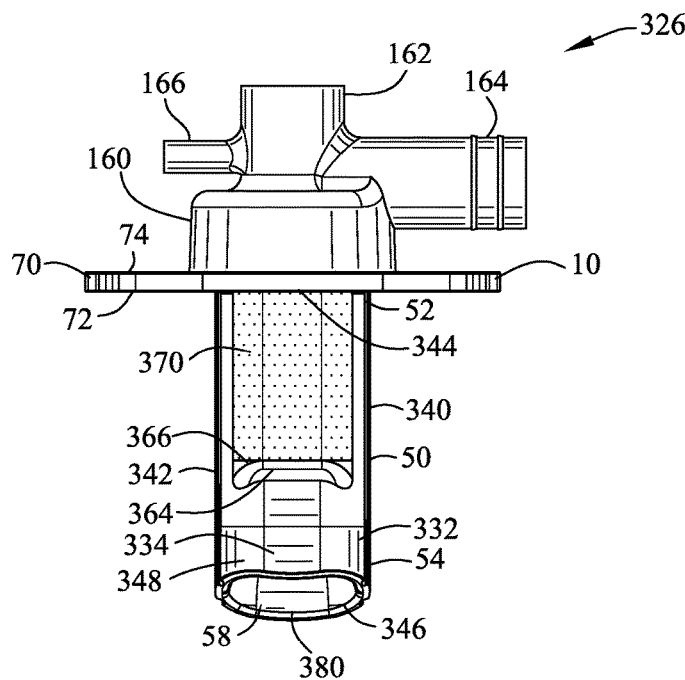
FIG. 78 is a front view of a sixth embodiment of the oropharyngeal device of the present invention.
Figure 79:
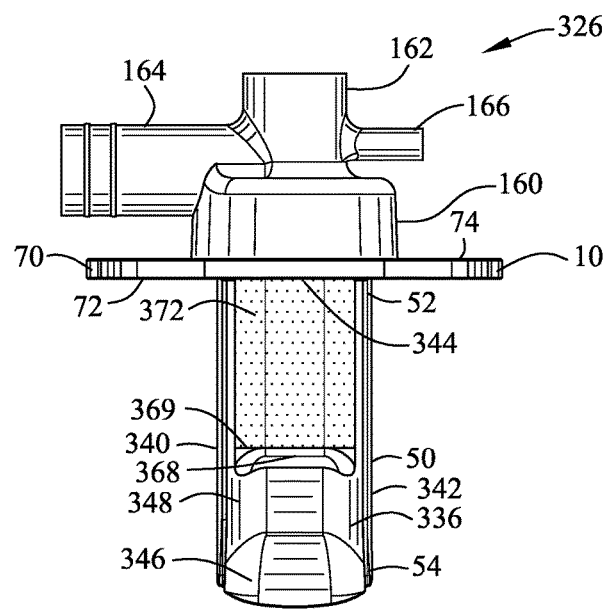
FIG. 79 is a rear view of FIG. 78.
Figure 80:
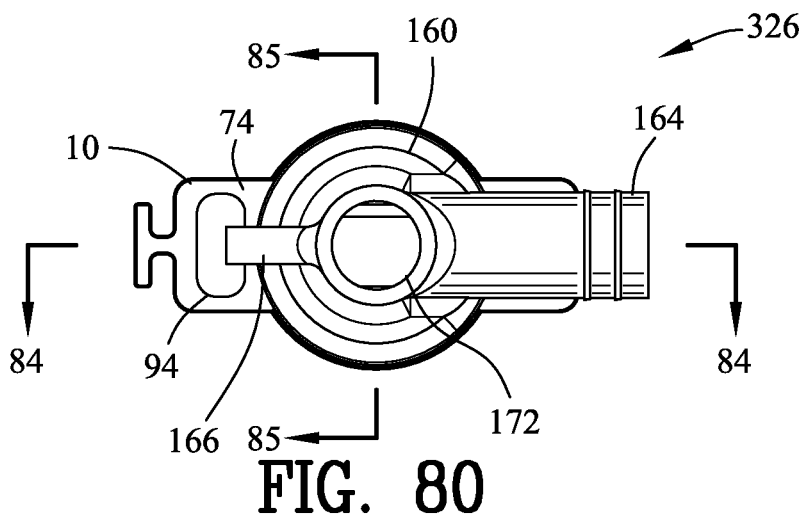
FIG. 80 is a top view of FIG. 78.
Figure 81:
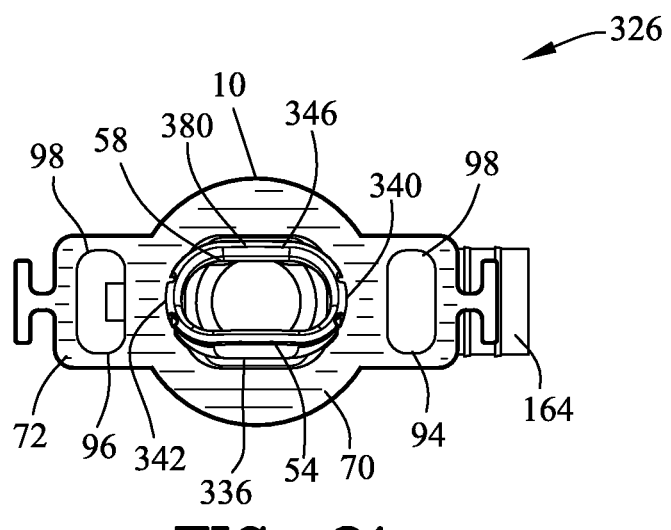
FIG. 81 is a bottom view of FIG. 78.
Figure 82:
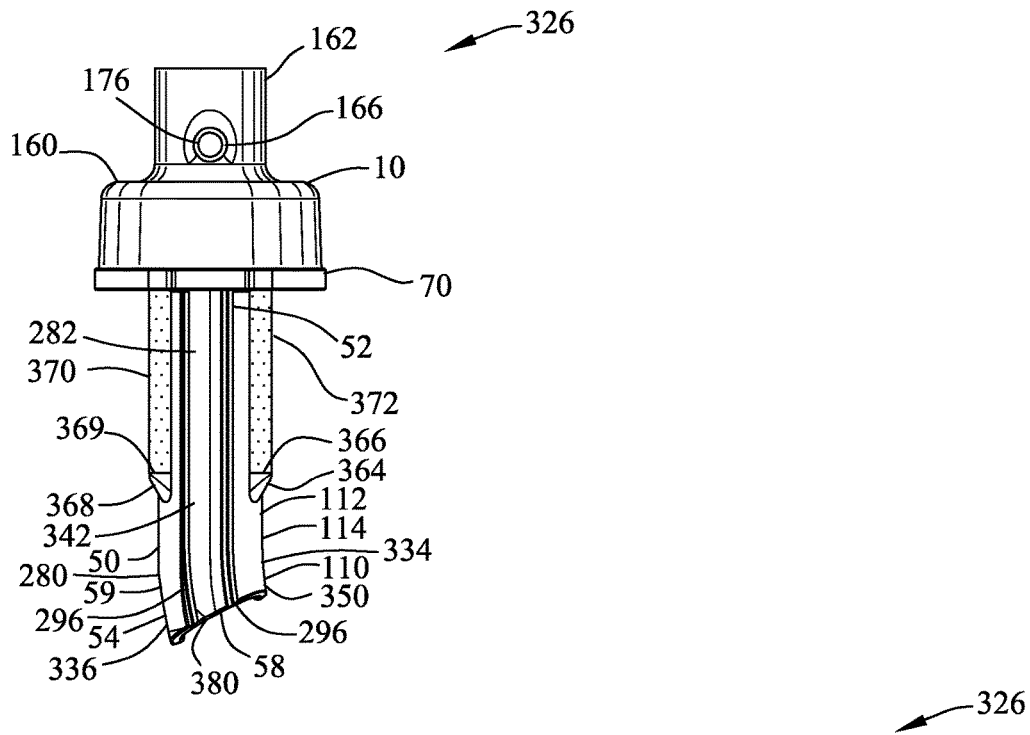
FIG. 82 is a left side view of FIG. 78.
Figure 83:
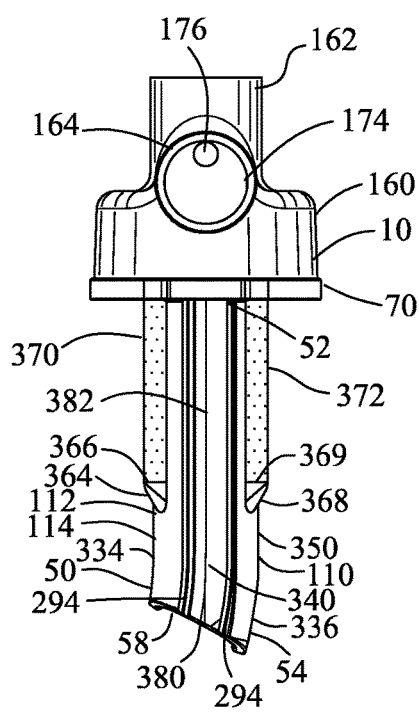
FIG. 83 is a right side view of FIG. 78.
Figure 84:
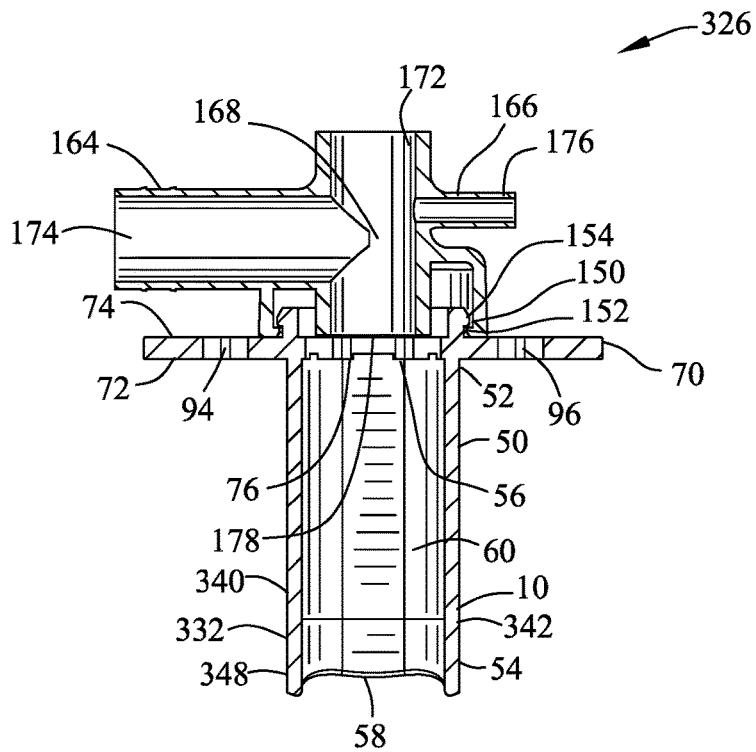
FIG. 84 is a sectional view along line 84-84 in FIG. 80.

As best shown in FIGS. 32, 33 and 51, the primary side wall 260 includes a primary groove 294 extending between the proximal end 52 and the distal end 54 for channeling saliva 46 through the primary groove 294 from the oral cavity 20 and adjacent to the proximal end 52 upon a suction 298 positioned adjacent to the proximal end 52. Similarly, the secondary side wall 262 includes a secondary groove 296 extending between the proximal end 52 and the distal end 54 for channeling saliva 46 through the secondary groove 296 from the oral cavity 20 and adjacent to the proximal end 52 upon the suction 298 positioned adjacent to the proximal end 52.

As best shown in FIGS. 28, 32, 33 and 47-49, the distal end 54 of the tubular member 50 includes an upper taper 300 in the upper wall 254, the primary side wall 260 and the secondary side wall 262 for defining an upper aperture 302 and permitting the elongated medical device 190, 192 to pivot in an ascending direction. The distal end 54 of the tubular member 50 includes a lower taper 304 in the lower wall 256, the primary side wall 260 and the secondary side wall 262 for defining a lower aperture 306 and permitting the elongated medical device 190, 192 to pivot in a descending direction. The upper aperture 302 and the lower aperture 306 define a second aperture area 308. The second aperture area 308 is greater than the constant rectangular cross-section 268 for permitting an elongated medical device 190, 192 to exit the distal end 54 of the tubular member 50.

The rectangular cross-section 252 of the tubular member 50 increases the contact area with the tongue 26 for maintaining airway patency and prevent the tongue from retracing in the upper airway. In addition, the rectangular cross-section 252 of the tubular member 50 has greater cross-sectional area for receiving larger elongated medical device 190, 192.

FIGS. 54-61 illustrate a third embodiment 320 of the present invention. FIGS. 62-69 illustrate a fourth embodiment 322 of the present invention. FIGS. 70-77 illustrate a fifth embodiment 324 of the present invention. FIGS. 78-85 illustrate a sixth embodiment 326 of the present invention.

The third embodiment 320, the fourth embodiment 322, the fifth embodiment 324 and the sixth embodiment 326 are similar to the first embodiment 48, however the third embodiment 320, the fourth embodiment 322, the fifth embodiment 324 and the sixth embodiment 326 include the tubular member 50 having a generally elliptical cross-section 332 for defining an upper wall 334, a lower wall 336, a primary arcuate side wall 340 and a secondary arcuate side wall 342. The primary aperture 56 defining a first elliptical area 344 and the secondary aperture 58 defining a second elliptical area 346. The first elliptical area 344 is equal to the second elliptical area 346 for defining a constant elliptical cross-section 348 of the tubular member 50 between the proximal end 52 and the distal end 54 for positioned adjacent to the epiglottis 28.

The third embodiment 320, the fourth embodiment 322, the fifth embodiment 324 and the sixth embodiment 326 include the arcuate shape 110 of said tubular member 50 defining a vertical dimension component 112 and a horizontal dimension component 114. In the third embodiment 320 and the fifth embodiment 324, the vertical dimension component 112 and the horizontal dimension component 114 define a generally one to one ratio 350 respectively. The length of the linear tubular member 282 and the arcuate shape 110 is generally equivalent.

In the fourth embodiment 322 and the sixth embodiment 326, the vertical dimension component 112 and the horizontal dimension component 114 defines a one to one ratio 350 respectively. The length of the linear tubular member 282 and the arcuate shape 110 is generally 50 to 1 ratio 272 respectively.

The tubular member 50 has an intermediate point 280 positioned between the proximal end 52 and the distal end 54. The tubular member 50 includes a linear tubular member 282 extending from the proximal end 52 and the intermediate point 280. The arcuate shape 59 extends from the intermediate point 280 to the distal end 54. The linear tubular member 282 increases the vertical dimension component 112 for positioning the distal end 54 of the tubular member 50 in a more close proximity to the epiglottis 28 and for depressing the tongue and maintaining airway patency between the oral cavity 20 and the epiglottis 28.

The upper wall 334 includes a first taper wall 364 for defining an upper channel 366 between the first taper wall 364 and the flange 70. A second taper wall 368 defines a lower channel 369 between the second taper wall 368 and the flange 70. A first deformable sheet 370 is positioned within the upper channel 366. A second deformable sheet 372 is positioned within the lower channel 369.

The first taper wall 364 and the second taper wall 368 engage the teeth 44 of the individual 24 for positioning the teeth 44 above said first deformable sheet 370 and the second deformable sheet 372 respectively. The first deformable sheet 370 and the second deformable sheet 374 engaging the teeth 44 of the individual 24 for preventing damaging the teeth 44 of the individual 24.

The secondary aperture 58 defines a generally elliptical aperture 380 in the upper wall 334, the lower wall 336, the primary arcuate side wall 340 and the secondary arcuate side wall 342. The secondary aperture 58 of the tubular member 50 defining a generally parallel orientation 382 relative to the linear tubular member 282 for permitting an elongated medical device 190, 192 to pivot in an ascending direction, a descending direction or a forward direction.

The third embodiment 320 as shown in FIGS. 54-61, is designed to enable gastroentrologists to perform endoscopic procedures under optimal conditions. The device 320 allows comfortable relaxation of mandibular (jaws) muscles as patient's teeth are gently pressing against the first deformable sheet 370 and the second deformable sheet 372 for protection. The oral cavity 20 is adequately secured with the tubular member 50 keeping the tongue 26 retracted to allow faster introduction of the endoscope. The gaseous aperture 174 of the manifold 160 allows insufflation of variable and titratable amounts of oxygen that will flow directly to as close as can be to the upper part of trachea. Carbon dioxide manometer 210 can be followed in a reverse direction from the gaseous measuring aperture 176 of the manifold 160. The device 320 has side grooves 294 and 296 to facilitate suctioning of saliva and (or) oral secretions throughout the procedure.

The device 320 is tightly fitted in the oral cavity 20 with a broad elastic band 100 that wraps around the back of the head 40. As this device 320 is securing the oral cavity 20 in an open position and enabling adequate flow of oxygen to the laryngeal area, it becomes easier to glide different types of endoscopes for variable gastroenterology procedures.

The fourth embodiment 322 as shown in FIGS. 62-69 is designed to enable cardiologists and anesthesiologist to perform trans esophageal echocardiogram examinations under optimal conditions. The device 322 allows comfortable relaxation of mandibular (jaws) muscles as patient's teeth are gently pressing against the first deformable sheet 370 and the second deformable sheet 372 for protection. The oral cavity 20 is adequately secured with the tubular member 50 keeping the tongue 26 retracted to allow faster introduction of the echocardiogram probe. The gaseous aperture 174 of the manifold 160 allows insufflation of variable and titratable amounts of oxygen that will flow directly to as close as can be to the upper part of trachea. Carbon dioxide manometer 210 can be followed in a reverse direction from the gaseous measuring aperture 176 of the manifold 160.

The device 322 has side grooves 294 and 296 to facilitate suctioning of saliva and (or) oral secretions throughout the procedure. The device is tightly fitted in the oral cavity 20 with the broad elastic band 100 that wraps around the back of the head 40.

The fifth embodiment 324 as shown in FIGS. 70-77 is for phenomenal secure laryngeal and bronchoscopic examinations. The device 324 allows comfortable relaxation of mandibular (jaws) muscles as patient's teeth are gently pressing against the first deformable sheet 370 and the second deformable sheet 372 for protection. The oral cavity 20 is adequately secured with the tubular member 50 keeping the tongue 26 retracted to allow faster introduction of the endoscope. Laryngoscopes can be gliding easily through the input device cylindrical body 162 to visualize the vocal cords and larynx for different procedures. All types of bronchoscopes can be introduced in a similar manner and can go further for endotracheal and bronchial examinations and procedures.

The gaseous aperture 174 of the manifold 160 allows insufflation of variable and titratable amounts of oxygen that will flow directly to as close as can be to the upper part of trachea. Carbon dioxide manometer 210 can be followed in a reverse direction from the gaseous measuring aperture 176 of the manifold 160. The device 324 has side grooves 294 and 296 to facilitate suctioning of saliva and (or) oral secretions throughout the procedure.

The device 324 is tightly fitted in the oral cavity 20 with a broad elastic band 100 that wraps around the back of the head 40. As this device 324 is securing the oral cavity 20 in an open position and enabling adequate flow of oxygen to the laryngeal area, it becomes exceptionally easier to glide different sizes of endotracheal tubes for orotracheal intubation. The device 324 secures oropharyngeal stabilization and patency with adequate delivery of oxygen flow until airway is intubated.

The sixth embodiment 326 as shown in FIGS. 78-85 is designed for stabilization of airways under different indications. The device 326 allows comfortable relaxation of mandibular (jaws) muscles as patient's teeth are gently pressing against the first deformable sheet 370 and the second deformable sheet 372 for protection. The oral cavity 20 is adequately secured with the tubular member 50 keeping the tongue 26 retracted to allow clearance and suctioning of airway secretions. Post sedation or anaethesia patients that are in need for periodic suctioning of airways with delivery of supplemental oxygen can benefit from this introduction. The device 326 can be used in emergency situation until able to intubate trachea for further interventions.

The gaseous aperture 174 of the manifold 160 allows insufflation of variable and titratable amounts of oxygen that will flow directly to as close as can be to the upper part of trachea. Carbon dioxide manometer 210 can be followed in a reverse direction from the gaseous measuring aperture 176 of the manifold 160. The device 326 has side grooves 294 and 296 to facilitate suctioning of saliva and (or) oral secretions throughout the procedure.

The device 326 is tightly fitted in the oral cavity 20 with a broad elastic band 100 that wraps around the back of the head 40. As this device 326 is the securing oral cavity 20 in an open position and enabling adequate flow of oxygen to the laryngeal area, it becomes beneficial for many patients that are not to be intubated i.e. those patients who are DNR or terminally ill. The peculiar feature of flavored material is a pleasant sensation for this category.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An oropharyngeal device for insertion into the oral cavity and the oropharynx of an individual, the oral cavity including a tongue and the oropharynx including an epiglottis, the oropharyngeal device, comprising:

a tubular member extending between a proximal end and a distal end;

said proximal end of said tubular member defining a primary aperture;

said distal end of said tubular member defining a secondary aperture;

said tubular member including a channel extending between said primary aperture and said secondary aperture;

a flange including a lower surface and an upper surface;

said lower surface of said flange coupled to said proximal end of said tubular member;

said flange including a flange aperture adjacent to said primary aperture;

said tubular member having a generally elliptical cross-section for defining an upper wall, a lower wall, a primary arcuate side wall and a secondary arcuate side wall;

said primary aperture defining a first elliptical area;

said secondary aperture defining a second elliptical area;

said first elliptical area being equal to said second elliptical area for defining a constant elliptical cross-section of said tubular member between said proximal end and said distal end;

said distal end adapted to be positioned adjacent to the epiglottis;

said tubular member defining an arcuate shape for depressing the tongue and maintaining airway patency between the oral cavity and the epiglottis;

a first wall coupled to said upper wall for defining an upper channel between said first wall and said flange;

a second wall coupled to said lower wall for defining a lower channel between said second wall and said flange;

a first deformable sheet positioned within said upper channel;

a second deformable sheet positioned within said lower channel;

said first wall defining a first taper body coupled to said upper wall;

said second wall defining a second taper body coupled to said lower wall;

said first taper body and said second taper body adapted to position the teeth on the first deformable sheet and the second deformable sheet;

an exterior channel external to the entire said tubular member and recessed within said primary arcuate side wall;

said exterior channel not fully enclosed along any portion of said exterior channel;

said exterior channel extending between said proximal end and said distal end for defining an elongated saliva input groove;

said elongated saliva input groove receiving saliva along the entire length of said tubular member and channeling saliva through said exterior channel from the oral cavity and adjacent to said proximal end upon a suction positioned adjacent to said proximal end;

and said primary arcuate side wall separating said first deformable sheet and said second deformable sheet;

said secondary arcuate side wall separating said first deformable sheet and said second deformable sheet;

and said exterior channel extending along said primary arcuate side wall and between said first deformable sheet and said second deformable sheet.

2. The oropharyngeal device for insertion into the oral cavity and the oropharynx of the individual as set forth in claim 1, wherein said arcuate shape of said tubular member defines a vertical dimension component and a horizontal dimension component; and said vertical dimension component and said horizontal dimension component defining a one to one ratio.

3. The oropharyngeal device for insertion into the oral cavity and the oropharynx of the individual as set forth in claim 1, further including an intermediate point positioned between said proximal end and said distal end;

said tubular member having a linear tubular member extending from said proximal end and said intermediate point;

said arcuate shape extending from said intermediate point to said distal end; and said linear tubular member positioning said distal end of said tubular member closer in proximity to the epiglottis.

4. The oropharyngeal device for insertion into the oral cavity and the oropharynx of the individual as set forth in claim 1, wherein said flange includes a first strap groove and a second strap groove;

said first strap groove and said second strap groove defining oppositely opposed positions relative to said flange aperture; and an elastic band engaging the first strap groove and the second strap groove for encircling the head or neck of the individual and maintaining said flange adjacent to the oral cavity of the individual.

5. The oropharyngeal device for insertion into the oral cavity and the oropharynx of the individual as set forth in claim 1, further including a manifold defining an input device aperture, a gaseous aperture and an output aperture;

said manifold coupled to said upper surface of said flange with said output aperture adjacent to said flange aperture;

said gaseous aperture providing a source of oxygen supplement through said tubular member and into the oral cavity; and a sphincter valve positioned within said input device aperture for permitting insertion of an elongated device through said tubular member and into the epiglottis and preventing loss of said source of oxygen supplement.

6. The oropharyngeal device for insertion into the oral cavity and the oropharynx of the individual as set forth in claim 1, further including a manifold defining an input device aperture, a gaseous measuring aperture and an output aperture;

said manifold coupled to said upper surface of said flange with said output aperture adjacent to said flange aperture;

said gaseous measuring aperture permitting the insertion of a carbon dioxide probe within said manifold for measuring the carbon dioxide being exhaled from the individual; and a sphincter valve positioned within said input device aperture for permitting insertion of an elongated device through said tubular member and into the epiglottis and preventing loss of a source of oxygen supplement.

7. The oropharyngeal device for insertion into the oral cavity and the oropharynx of the individual as set forth in claim 1, wherein said upper surface of said flange includes a circular locking rim;

a manifold including an input device cylindrical body, a gaseous cylindrical body, a gaseous measuring cylindrical body and a main cylindrical body;

said input device cylindrical body defining an input device aperture;

said gaseous cylindrical body defining a gaseous aperture;

said gaseous measuring cylindrical body defining a gaseous measuring aperture;

said main cylindrical body defining an output aperture;

said manifold including a locking cap for engaging with said circular locking rim with said output aperture adjacent to said flange aperture and permitting a rotational displacement of said manifold relative to said flange;

said gaseous aperture adapted to provide a source of oxygen supplement through said tubular member and into the oral cavity;

said gaseous measuring aperture permitting insertion of a carbon dioxide probe within said manifold for measuring the carbon dioxide being exhaled from the individual; and a sphincter valve positioned within said input device aperture for permitting insertion of an elongated device through said tubular member and into the epiglottis and preventing loss of said source of oxygen supplement.

8. The oropharyngeal device for insertion into the oral cavity and the oropharynx of the individual as set forth in claim 1, wherein said secondary aperture defines a generally elliptical aperture in said upper wall, said lower wall, said primary arcuate side wall and said secondary arcuate side wall; and said secondary aperture of said tubular member defining a generally parallel orientation relative to said linear tubular member for permitting an elongated medical device to pivot in an ascending direction, a descending direction or a forward direction.

9. An oropharyngeal device for insertion into the oral cavity and the oropharynx of an individual, the oral cavity including a tongue and the oropharynx including an epiglottis, the oropharyngeal device, comprising:

a tubular member extending between a proximal end and a distal end;

said proximal end of said tubular member defining a primary aperture;

said distal end of said tubular member defining a secondary aperture;

said tubular member including a channel extending between said primary aperture and said secondary aperture;

a flange including a lower surface and an upper surface;

said lower surface of said flange coupled to said proximal end of said tubular member;

said flange including a flange aperture adjacent to said primary aperture;

said tubular member having a generally elliptical cross-section for defining an upper wall, a lower wall, a primary arcuate side wall and a secondary arcuate side wall;
said primary aperture defining a first elliptical area;
said secondary aperture defining a second elliptical area;
said first elliptical area being equal to said second elliptical area for defining a constant elliptical cross-section of said tubular member between said proximal end and said distal end;
said distal end adapted to be positioned adjacent to the epiglottis;
said tubular member defining an arcuate shape for depressing the tongue and maintaining airway patency between the oral cavity and the epiglottis;
an exterior channel external to the entire said tubular member and recessed within said primary arcuate side wall;
said exterior channel not fully enclosed along any portion of said exterior channel;
said exterior channel extending between said proximal end and said distal end for defining an elongated saliva input groove; and
said elongated saliva input groove receiving saliva along the entire length of said tubular member and channeling saliva through said exterior channel from the oral cavity and adjacent to said proximal end upon a suction positioned adjacent to said proximal end.

10. The oropharyngeal device for insertion into the oral cavity and the oropharynx of the individual as set forth in claim 9, further including a secondary exterior channel external to the entire said tubular member and recessed within said secondary arcuate side wall;
said secondary exterior channel extending between said proximal end and said distal end for defining a secondary elongated saliva input groove; and
said secondary elongated saliva input groove receiving saliva along the entire length of said tubular member and channeling saliva through said secondary exterior channel from the oral cavity and adjacent to said proximal end upon said suction positioned adjacent to said proximal end.

11. An oropharyngeal device for insertion into the oral cavity and the oropharynx of an individual, the oral cavity including a tongue and the oropharynx including an epiglottis, the oropharyngeal device, comprising:
a tubular member extending between a proximal end and a distal end;
said proximal end of said tubular member defining a primary aperture;
said distal end of said tubular member defining a secondary aperture;
said tubular member including a channel extending between said primary aperture and said secondary aperture;
a flange including a lower surface and an upper surface;
said lower surface of said flange coupled to said proximal end of said tubular member;
said flange including a flange aperture adjacent to said primary aperture;
said tubular member defining an arcuate shape for depressing the tongue and maintaining airway patency between the oral cavity and the epiglottis;
a first wall coupled to an upper wall for defining an upper channel between said first wall and said flange;
a second wall coupled to a lower wall for defining a lower channel between said second wall and said flange;
a first deformable sheet positioned within said upper channel;
a second deformable sheet positioned within said lower channel;
said first deformable sheet and said second deformable sheet adapted to engage the teeth of the individual;
an exterior channel external to the entire said tubular member and recessed within a primary arcuate side wall of said tubular member;
said exterior channel not fully enclosed along any portion of said exterior channel;
said exterior channel extending between said proximal end and said distal end for defining an elongated saliva input groove; said elongated saliva input groove receiving saliva along the entire length of said tubular member and channeling saliva through said exterior channel from the oral cavity and adjacent to said proximal end upon a suction positioned adjacent to said proximal end;
said primary arcuate side wall separating said first deformable sheet and said second deformable sheet;
a secondary arcuate side wall separating said first deformable sheet and said second deformable sheet; and
said exterior channel extending along said primary arcuate side wall and between said first deformable sheet and said second deformable sheet.

12. An oropharyngeal device for insertion into the oral cavity and the oropharynx of an individual, the oral cavity including, a tongue and the oropharynx including an epiglottis, the oropharyngeal device, comprising:
a tubular member extending between a proximal end and a distal end;
said proximal end of said tubular member defining a primary aperture;
said distal end of said tubular member defining a secondary aperture;
said tubular member including a channel extending between said primary aperture and said secondary aperture;
a flange including a lower surface and an upper surface;
said lower surface of said flange coupled to said proximal end of said tubular member;
said flange including a flange aperture adjacent to said primary aperture;
said tubular member defining an arcuate shape for depressing the tongue and maintaining airway patency between the oral cavity and the epiglottis;
an exterior channel external to the entire said tubular member and recessed within a side wall of said tubular member;
said exterior channel not fully enclosed along any portion of said exterior channel;
said exterior channel extending between said proximal end and said distal end for defining an elongated saliva input groove; and
said elongated saliva input groove receiving saliva along the entire length of said tubular member and channeling saliva through said exterior channel from the oral cavity and adjacent to said proximal end upon a suction positioned adjacent to said proximal end.

\* \* \* \* \*